US012594278B2

(12) United States Patent
Jaiswal et al.

(10) Patent No.: US 12,594,278 B2
(45) Date of Patent: Apr. 7, 2026

(54) METHOD FOR TREATMENT OF MUSCULAR DYSTROPHY

(71) Applicant: CHILDREN'S NATIONAL MEDICAL CENTER, Washington, DC (US)

(72) Inventors: Jyoti Jaiswal, Rockville, MD (US); Marshall Hogarth, Washington, DC (US)

(73) Assignee: CHILDREN'S NATIONAL MEDICAL CENTER, Washington, DC (US)

(*) Notice: Subject to any disclaimer, the term of this patent is extended or adjusted under 35 U.S.C. 154(b) by 1117 days.

(21) Appl. No.: 17/627,203

(22) PCT Filed: Jul. 16, 2020

(86) PCT No.: PCT/US2020/042285

§ 371 (c)(1),
(2) Date: Jan. 14, 2022

(87) PCT Pub. No.: WO2021/011747

PCT Pub. Date: Jan. 21, 2021

(65) Prior Publication Data

US 2022/0257606 A1 Aug. 18, 2022

Related U.S. Application Data

(60) Provisional application No. 62/874,607, filed on Jul. 16, 2019.

(51) Int. Cl.

| | |
|---|---|
| ***A61K 31/5415*** | (2006.01) |
| ***A61K 45/06*** | (2006.01) |
| ***A61P 21/00*** | (2006.01) |

(52) U.S. Cl.

CPC .......... *A61K 31/5415* (2013.01); *A61K 45/06* (2013.01); *A61P 21/00* (2018.01); *A61K 2121/00* (2013.01)

(58) Field of Classification Search

CPC .................................................. A61K 31/5415
USPC ...................................................... 514/224.2
See application file for complete search history.

(56) References Cited

U.S. PATENT DOCUMENTS

| | | |
|---|---|---|
| 4,342,566 A | 8/1982 | Theofilopoulos et al. |
| 5,804,440 A | 9/1998 | Burton et al. |
| 6,096,441 A | 8/2000 | Barbas et al. |

FOREIGN PATENT DOCUMENTS

| | | |
|---|---|---|
| WO | 94/29348 | 12/1994 |
| WO | 2018227134 A1 | 12/2018 |
| WO | 2020020857 A1 | 1/2020 |

OTHER PUBLICATIONS

International Search Report and Written Opinion in PCT/US2020/042285. Mailed Oct. 26, 2020. 8 pages.
Hogarth et al. 'Fibroadipogenic progenitors are responsible for muscle loss in limb girdle muscular dystrophy 2B', Nature Communications, Jun. 3, 2019 (Jun. 3, 2019), vol. 10, pp. 1-13.
International Preliminary Report on Patent ability issued for Application No. PCT/US2020/042285, dated Jan. 27, 2022.
Zoller, Mark J., and Michael Smith. "Oligonucleotide-directed mutagenesis using M13-derived vectors: an efficient and general procedure for the production of point mutations in any fragment of DNA." Nucleic Acids Research 10.20 (1982): 6487-6500.
Köhler, Georges, and Cesar Milstein. "Continuous cultures of fused cells secreting antibody of predefined specificity." nature 256.5517 (1975): 495-497.
Zoller, Mark J. "New recombinant DNA methodology for protein engineering." Current opinion in biotechnology 3.4 (1992): 348-354.

*Primary Examiner* — Raymond J Henley, III
(74) *Attorney, Agent, or Firm* — Meunier Carlin & Curfman LLC

(57) ABSTRACT

Disclosed herein are compositions that inhibit adipogenesis of a fibro/adipogenic precursor (FAP) cell and methods relating to treating, preventing, reducing, and/or inhibiting a muscular degenerative condition a muscular degenerative condition comprising administering said inhibitors.

14 Claims, 14 Drawing Sheets

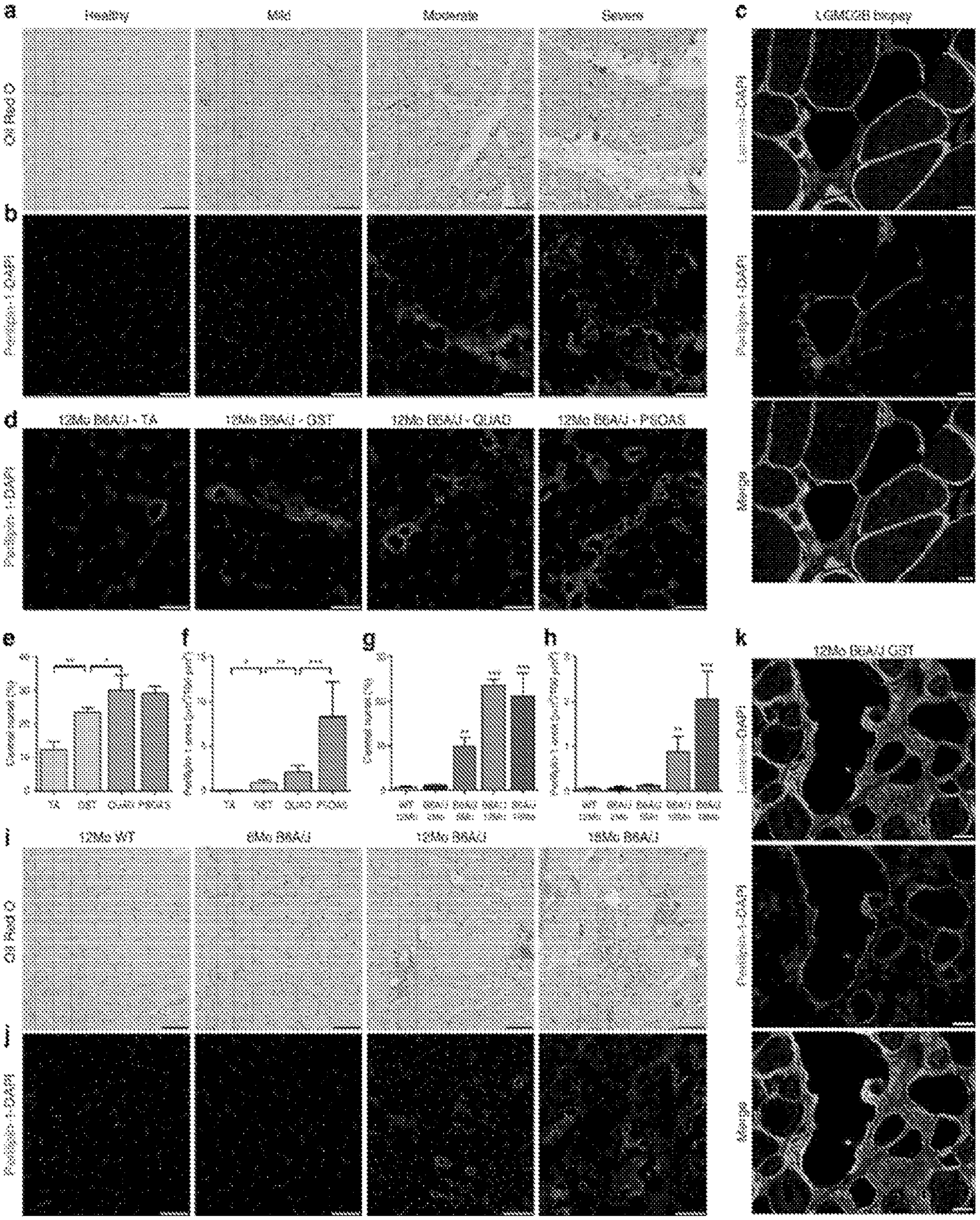
FIG. 1A, FIG. 1B, FIG. 1C, FIG. 1D, FIG. 1E, FIG. 1F, FIG. 1G, FIG. 1H, FIG. 1I, and FIG. 1J

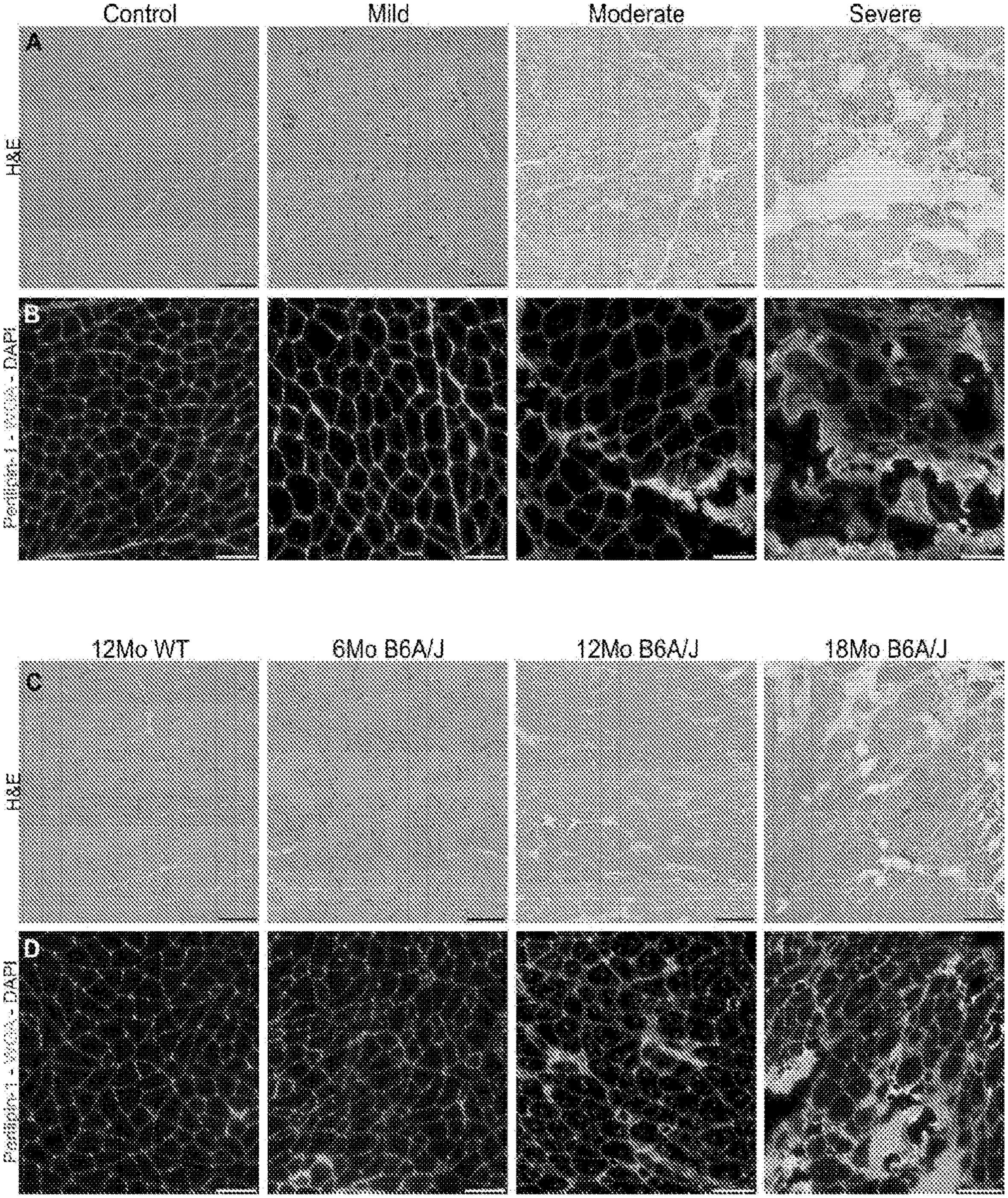
FIG. 2A, FIG. 2B, FIG. 2C, and FIG. 2D

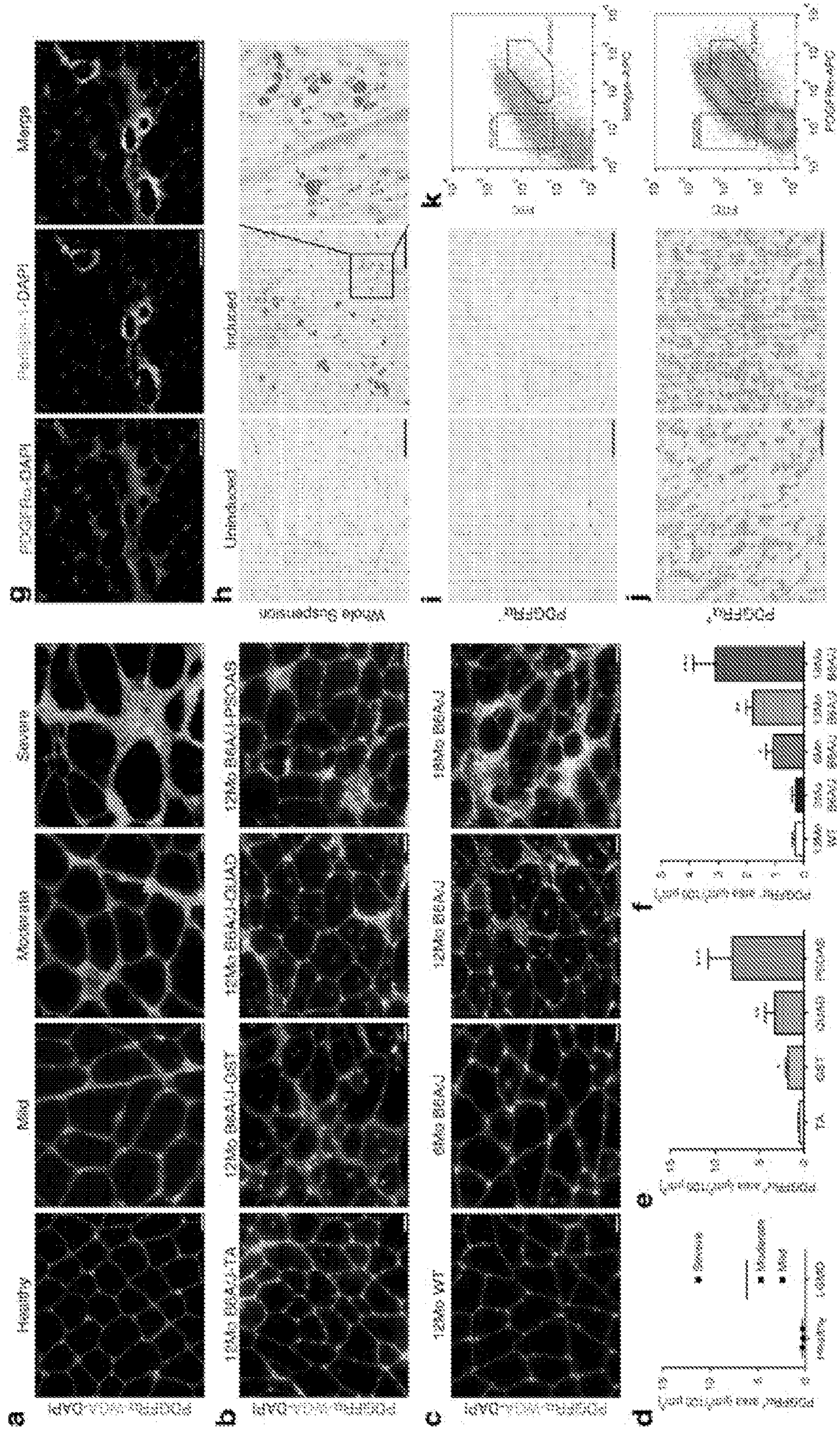
FIG. 3A, FIG. 3B, FIG. 3C, FIG. 3D, FIG. 3E, FIG. 3F, FIG. 3G, FIG. 3H, FIG. 3I, FIG. 3J, and FIG. 3K

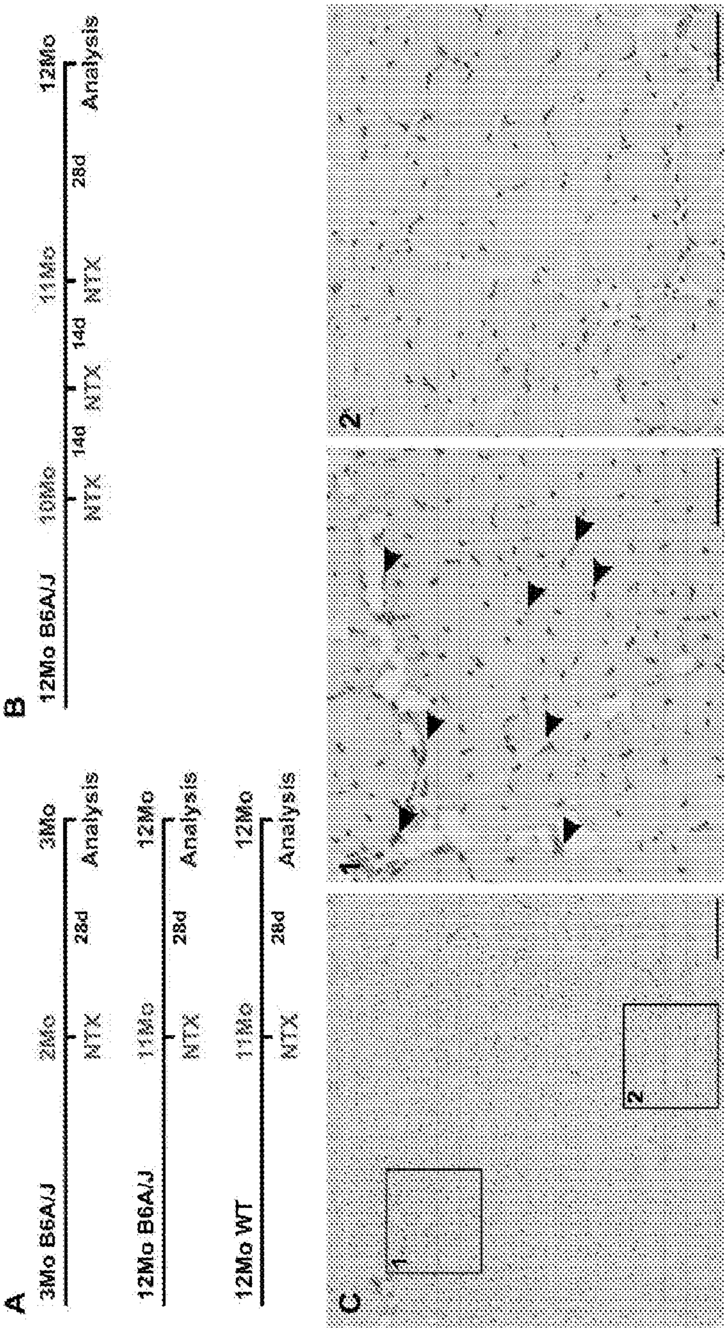
FIG. 5A, FIG. 5B, and FIG. 5C

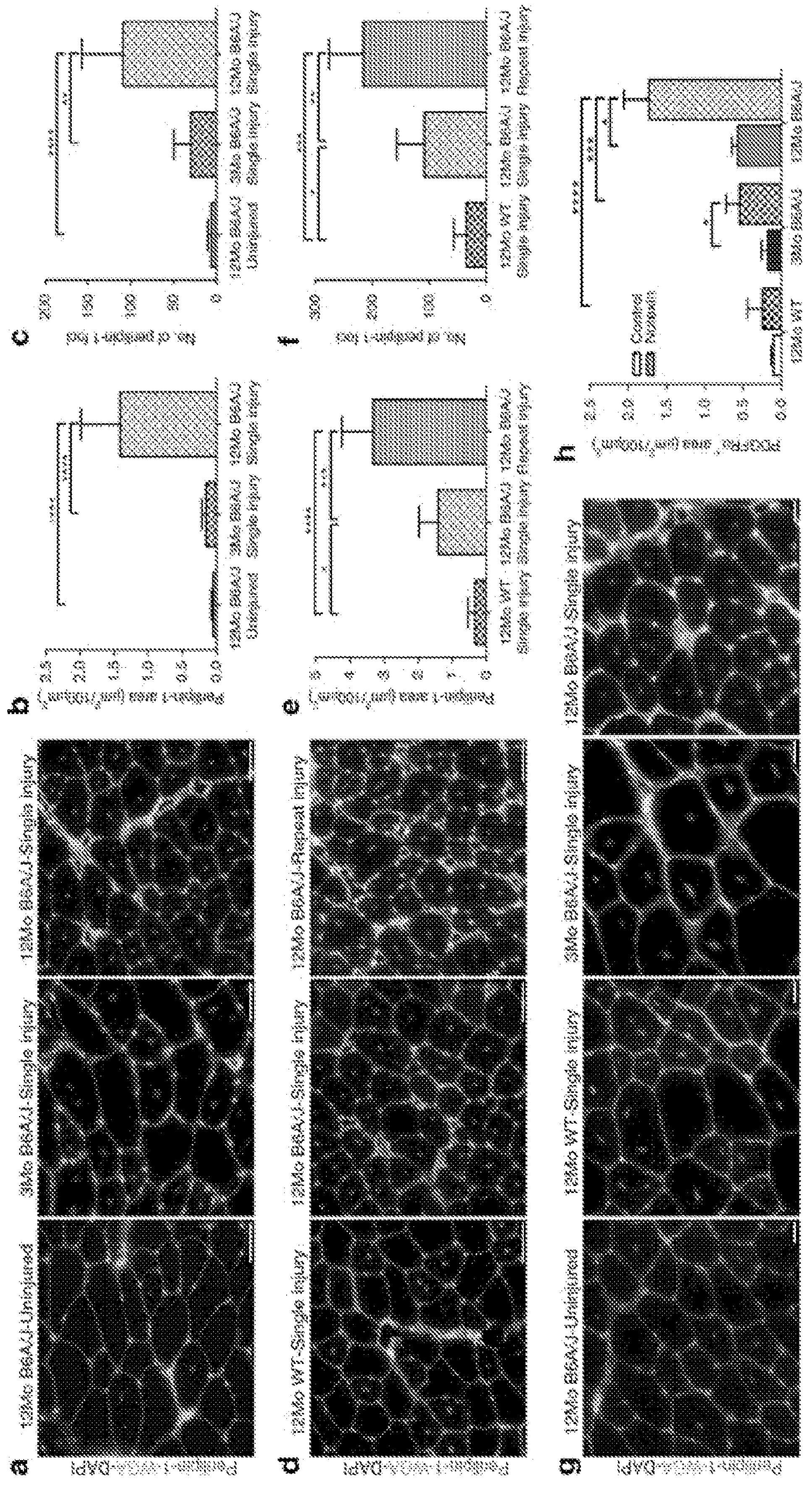
FIG. 6A, FIG. 6B, FIG. 6C, FIG. 6D, FIG. 6E, FIG. 6F, FIG. 6G, and FIG. 6H

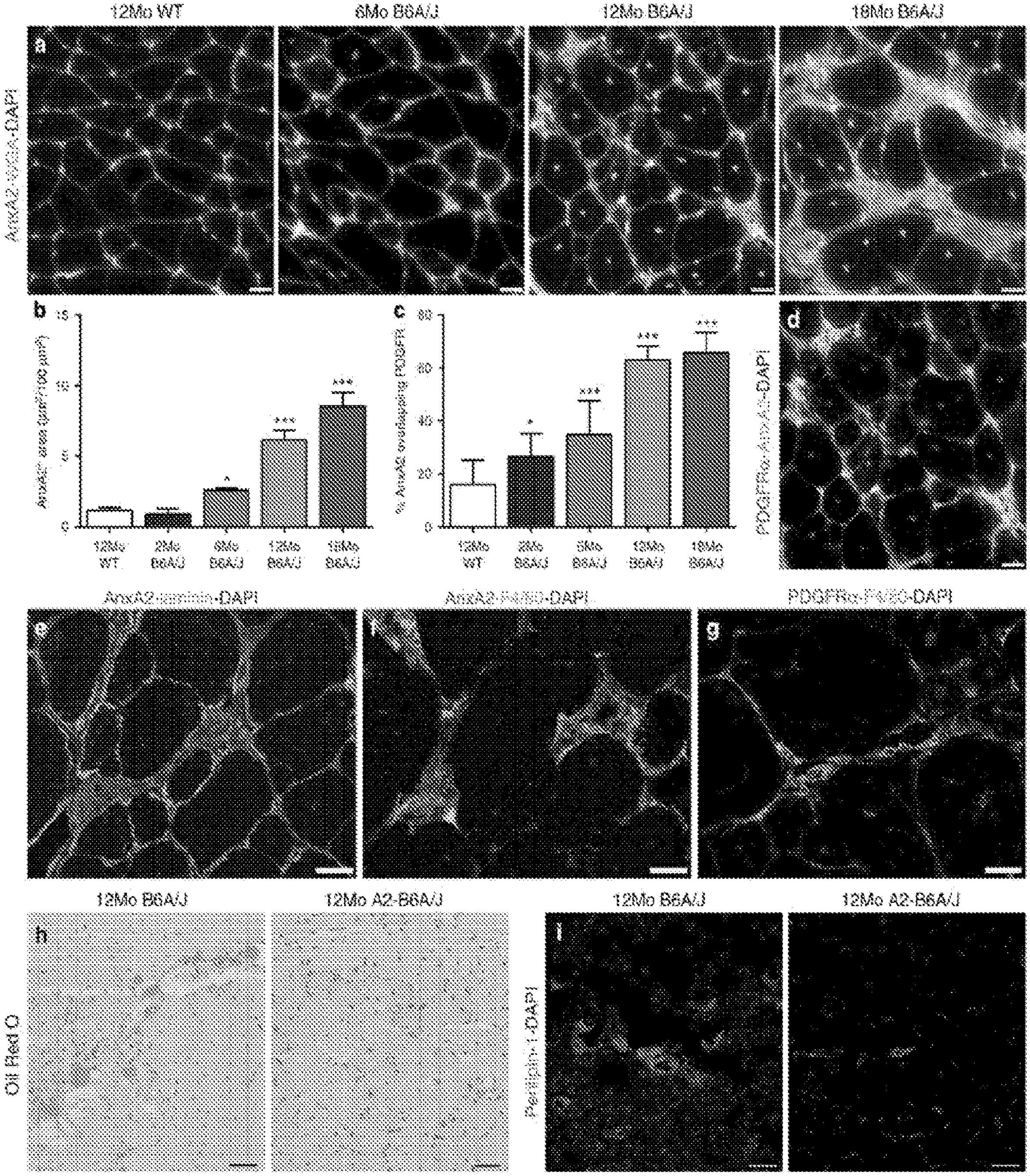
FIG. 7A, FIG. 7B, FIG. 7C, FIG. 7D, FIG. 7E, FIG. 7F, FIG. 7G, FIG. 7H, and FIG. 7I

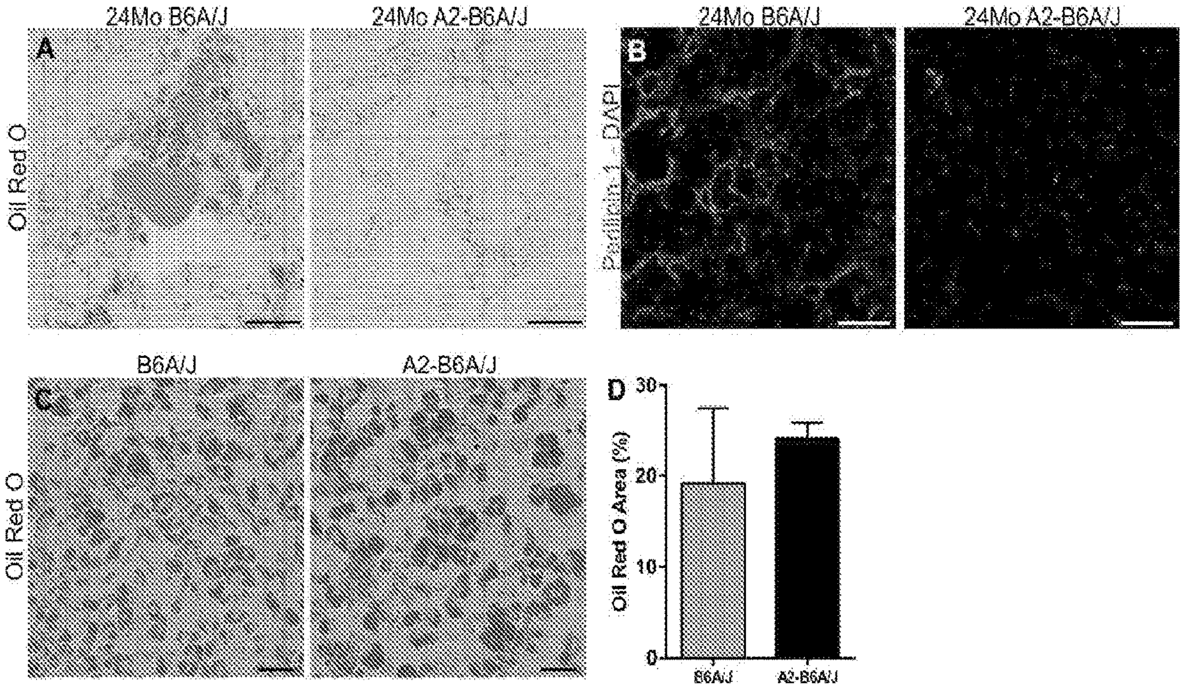
FIG. 8A, FIG. 8B, FIG. 8C, and FIG. 8D

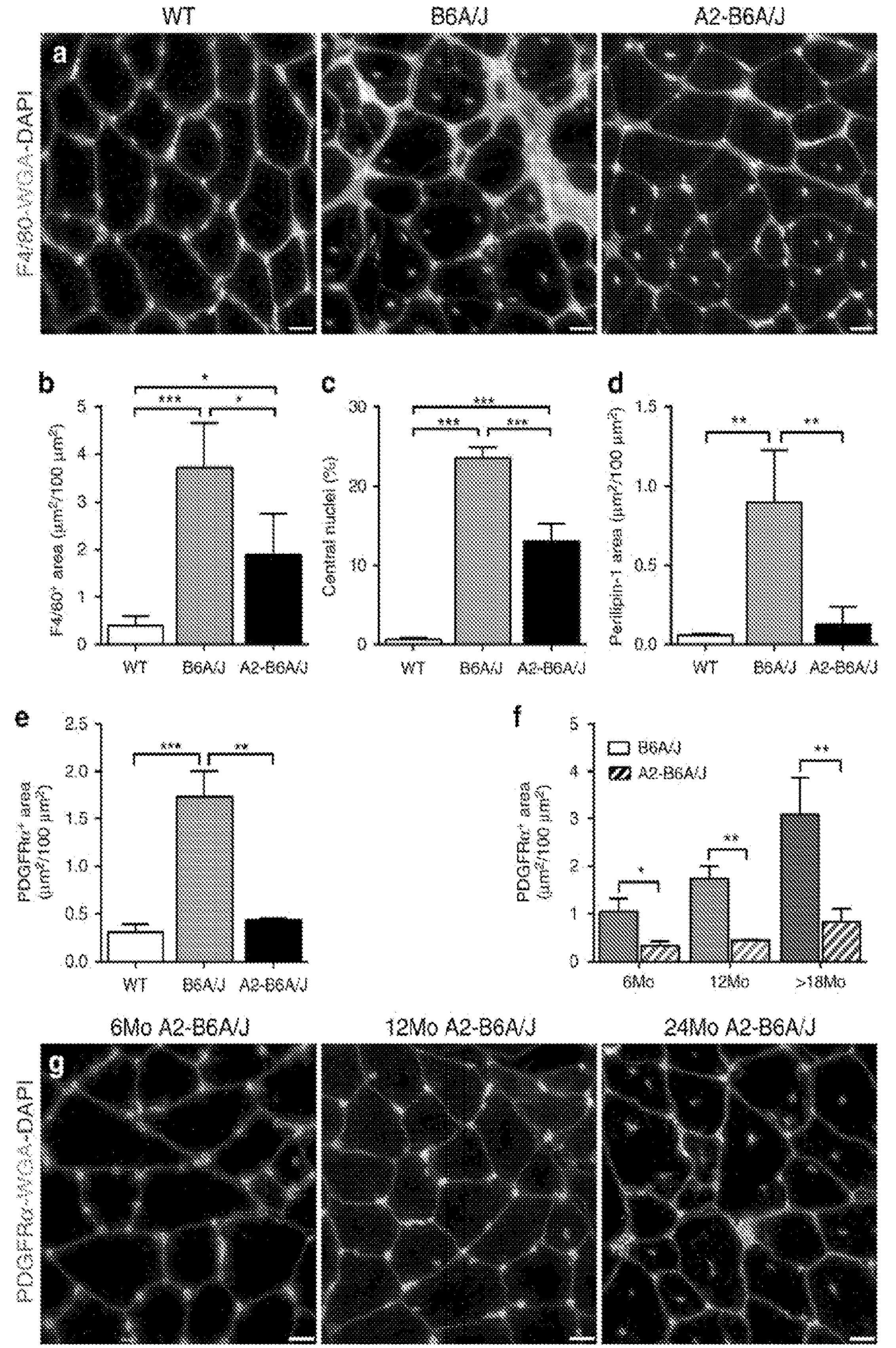
FIG. 9A, FIG. 9B, FIG. 9C, FIG. 9D, FIG. 9E, FIG. 9F, and FIG. 9G

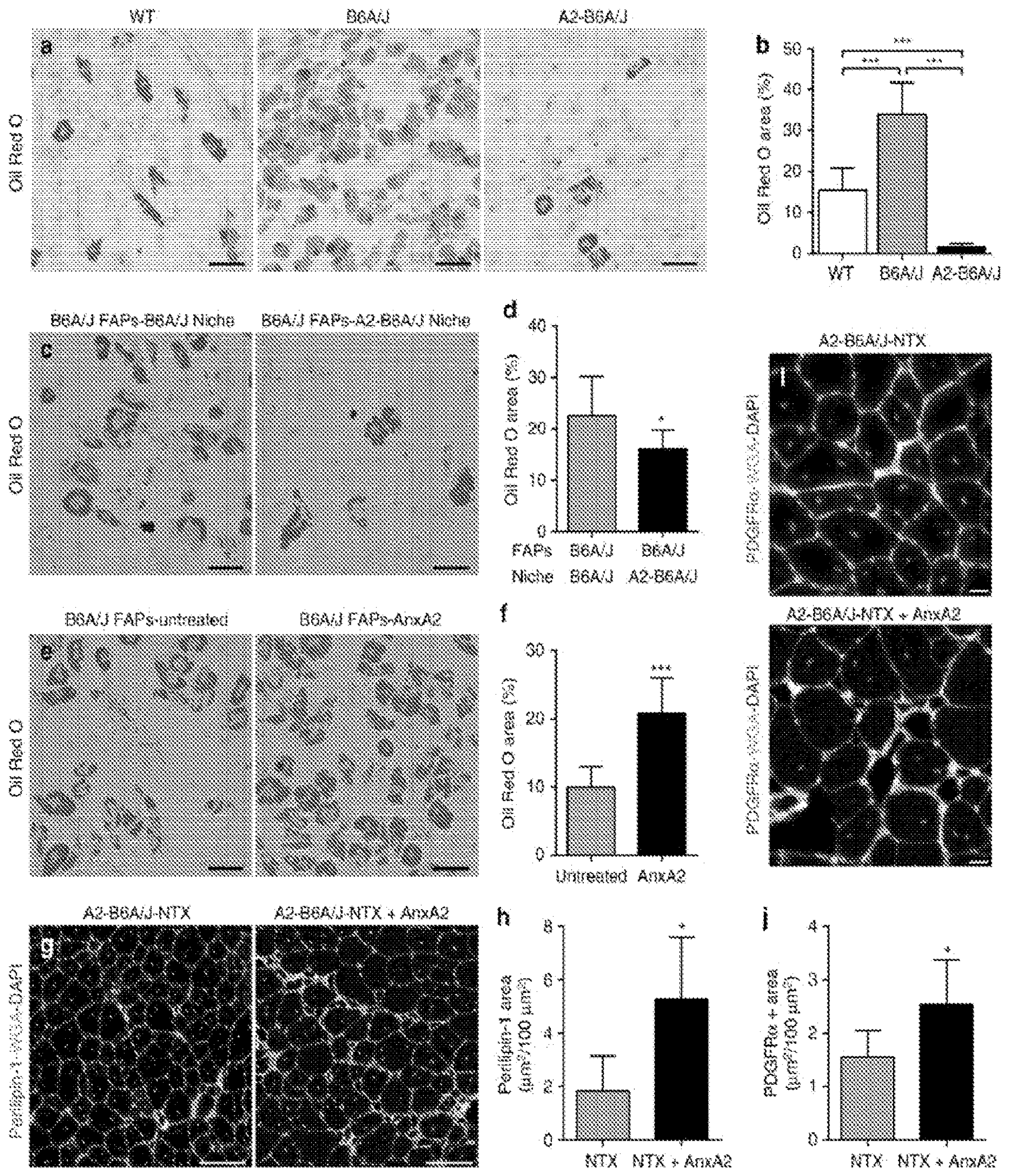
FIG. 10A, FIG. 10B, FIG. 10C, FIG. 10D, FIG. 10E, FIG. 10F, FIG. 10G, FIG. 10H, FIG. 10I, and FIG. 10J

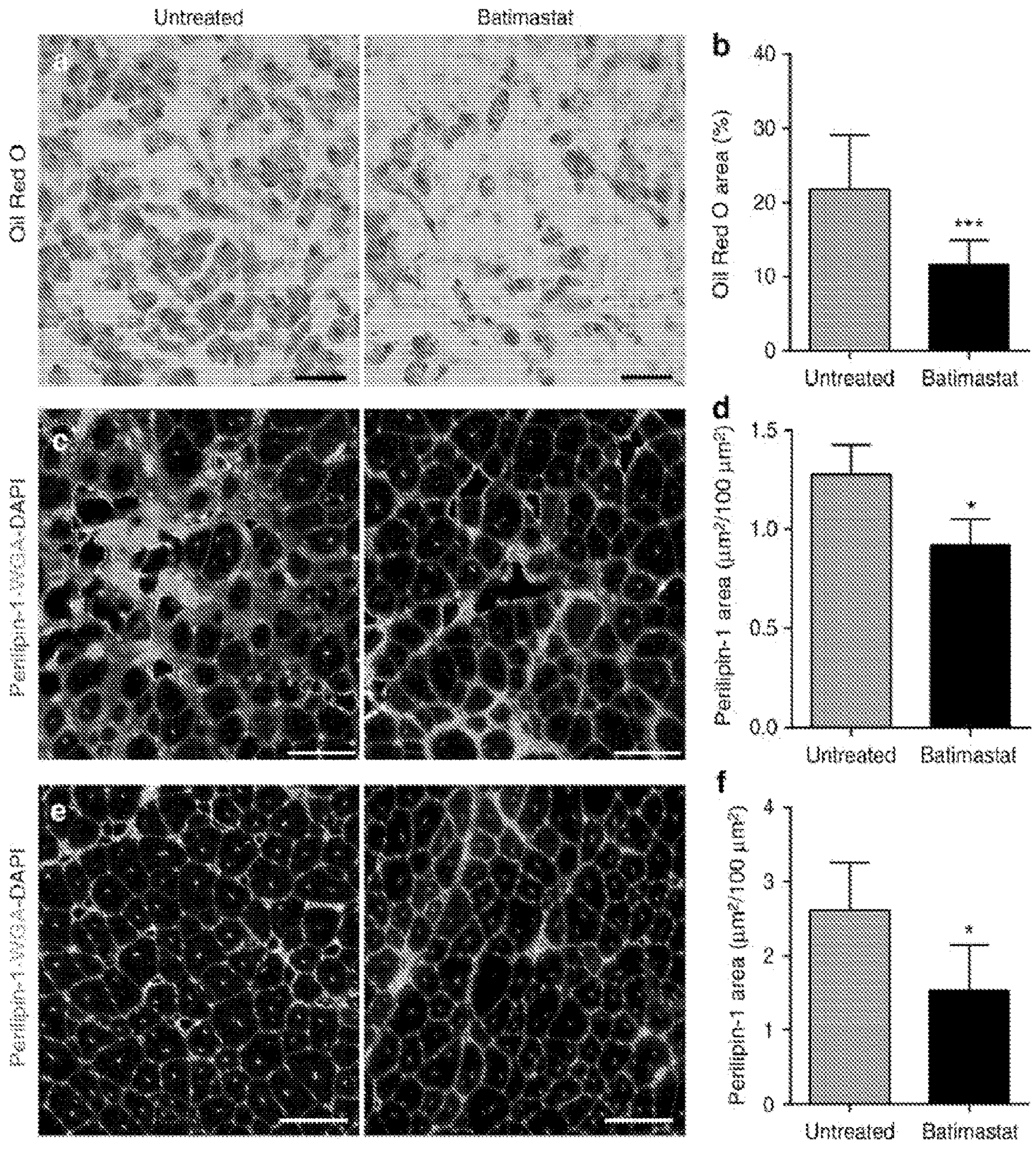
FIG. 11A, FIG. 11B, FIG. 11C, FIG. 11D, FIG. 11E, and FIG. 11F

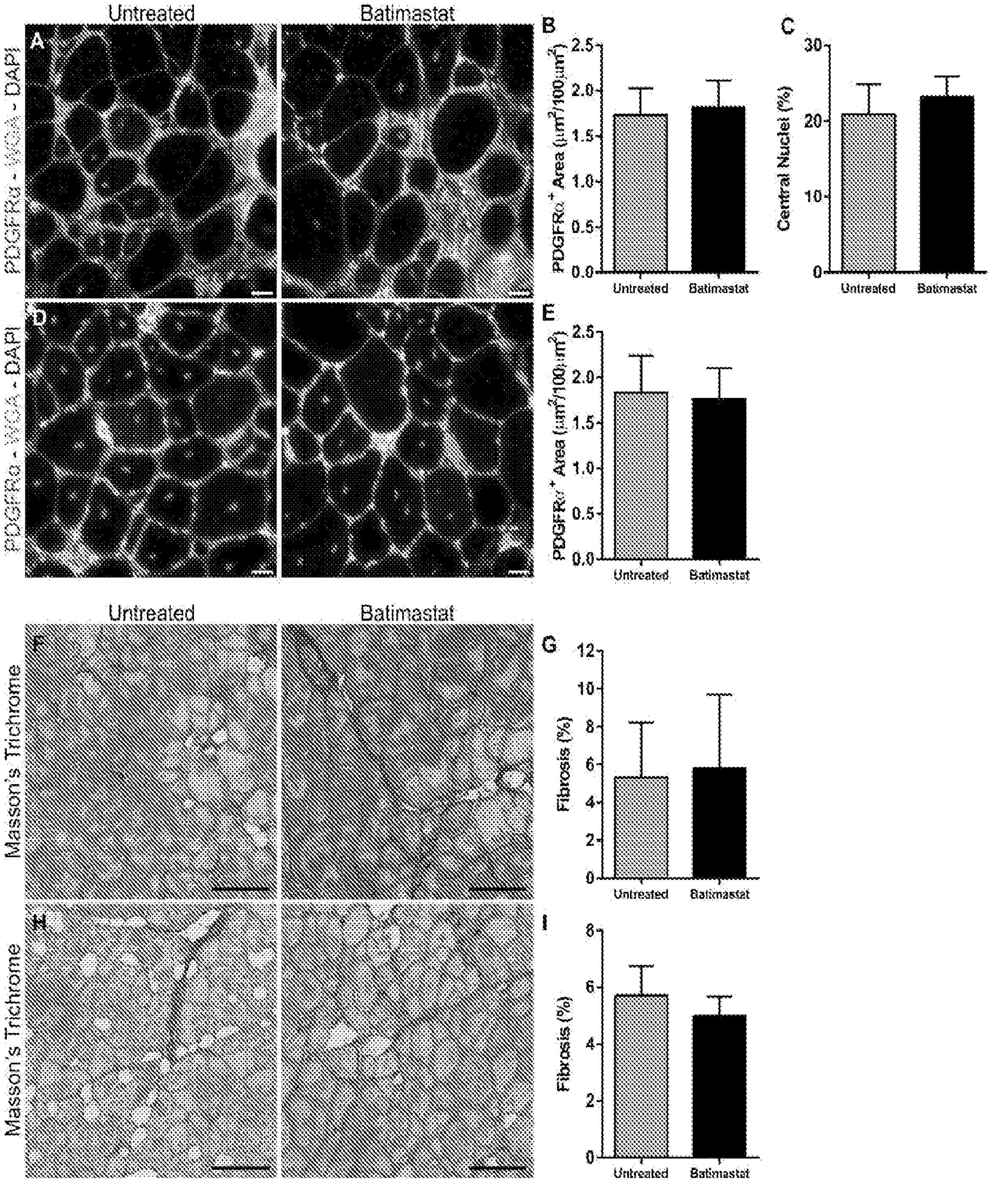
FIG. 12A, FIG. 12B, FIG. 12C, FIG. 12D, FIG. 12E, FIG. 12F, FIG. 12G, FIG. 12H, and FIG. 12I

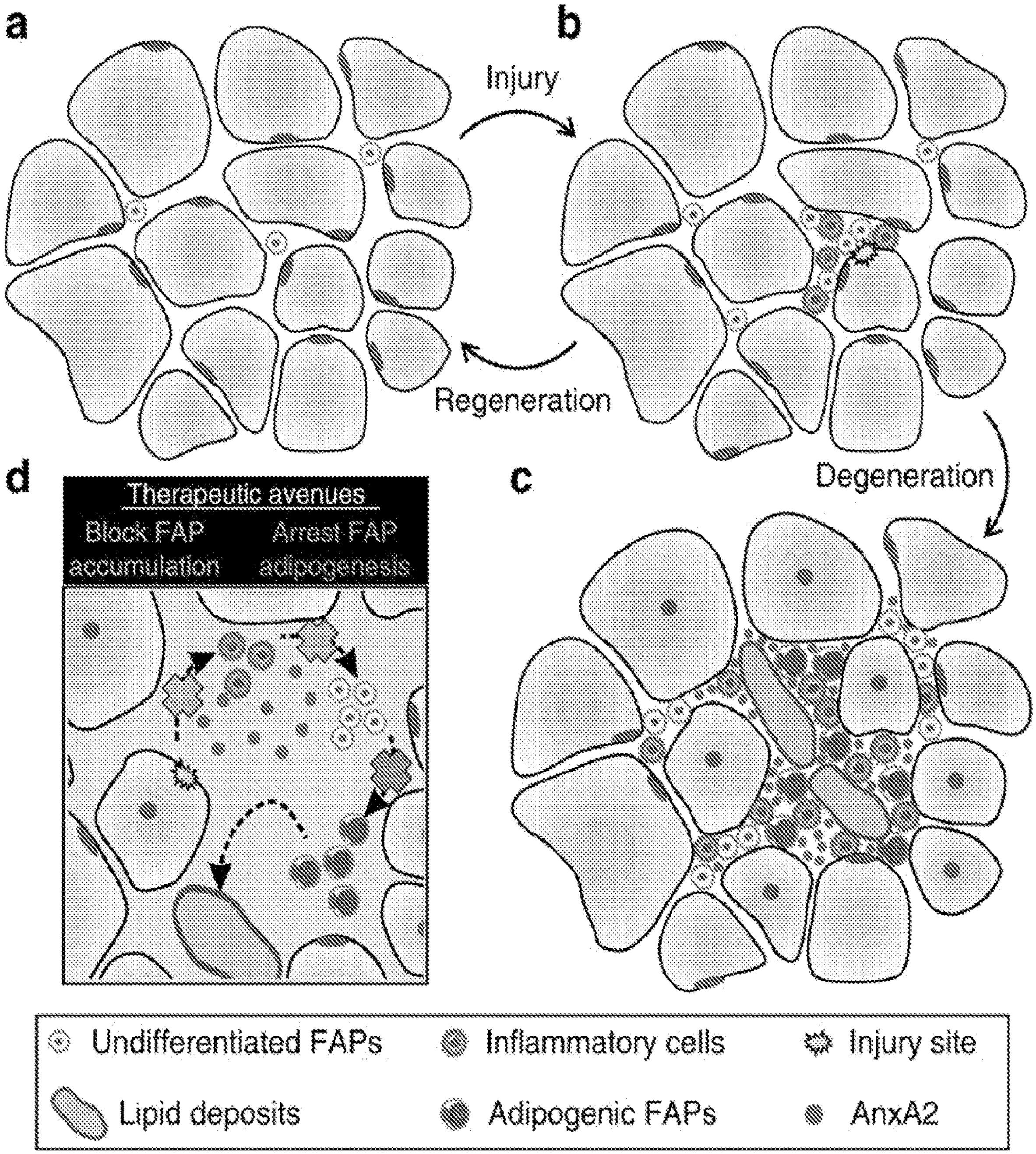
FIG. 13A, FIG. 13B, FIG. 13C, and FIG. 13D

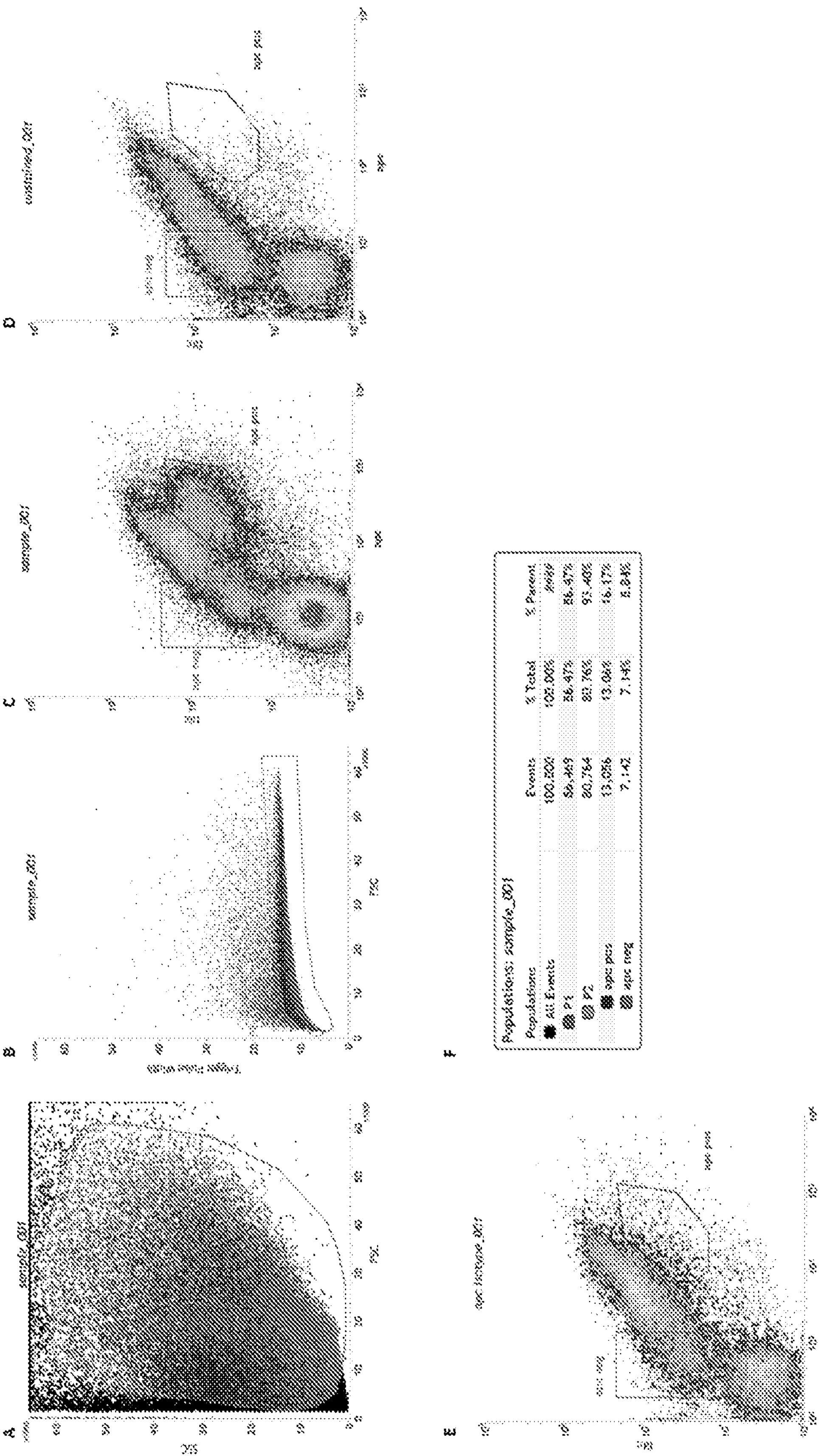
FIG. 14A, FIG. 14B, FIG. 14C, FIG. 14D, FIG. 14E, and FIG. 14F

METHOD FOR TREATMENT OF MUSCULAR DYSTROPHY

CLAIM TO PRIORITY

This application is a United States National Phase Patent Application of International Patent Application Number PCT/US2020/042285, filed on Jul. 16, 2020, which claims the benefit of U.S. Provisional Application No. 62/874,607, filed on Jul. 16, 2019, applications which are incorporated herein by reference in their entireties.

STATEMENT REGARDING FEDERALLY SPONSORED RESEARCH OR DEVELOPMENT

This invention was made with Government Support under Grant NOs: R01AR055686, K260D011171, R24HD050846, P50AR060836, and U54HD090257 awarded by the National Institutes of Health. The Government has certain rights in the invention.

BACKGROUND

Although composed of terminally differentiated multinucleated myofibers, adult skeletal muscle maintains a remarkable ability to regenerate from injury. This ability depends on mono-nucleated cells that reside amongst the skeletal myofibers and those that enter the muscle following injury. With the ability of the satellite cells to proliferate and fuse to regenerate damaged myofibers, they have long been identified as the primary driver of regeneration. Accordingly, ablating the Pax7+ satellite cells in adult mice blocks myofiber regeneration. However, there is growing evidence that myofiber regeneration involves complex multicellular and extracellular matrix interactions creating a regenerative niche that consists of secreted factors, immune cells, myogenic and non-myogenic progenitors.

FAPs are muscle-resident non-myogenic progenitors of mesenchymal origin that are marked by cell surface expression of platelet-derived growth factor receptor alpha (PDGFRa) that proliferate in response to injury and can undergo fibrogenic or adipogenic differentiation. Muscle injury triggers an acute myofiber repair response, failure of which causes myofiber death and resulting tissue infiltration by inflammatory cells. These cells help clear the debris from the injury site and activate both satellite cell and FAP proliferation. A critical element in the regenerative process is transition of the pro-inflammatory cells to become pro-regenerative within 2-3 days after injury. This coincides with the apoptotic clearance of FAPs and with satellite cell fusion leading to myogenesis. Timely occurrence of the above cellular choreography between inflammatory, fibro/adipogenic, and satellite cells has been implicated in successful muscle regeneration. Consequently, disrupting inflammatory infiltration and FAP homeostasis impairs regeneration, resulting in fibrotic and adipogenic degeneration of injured muscle.

Adipogenic differentiation of FAPs has been implicated in muscle loss following rotator cuff injury in mice. While adipogenic muscle replacement is prevalent in muscular dystrophies, it remains to be determined if FAPs are responsible for this. The dysferlinopathies represent a heterogeneous group of late-onset muscle disease, including limb girdle muscular dystrophy type 2B (LGMD2B), which are caused by mutations in the dysferlin gene. Lack of dysferlin compromises myofiber repair, alters calcium homeostasis, and causes chronic muscle inflammation. However, these deficits do not explain the late and abrupt disease onset, progressive nature, or specific muscle involvement seen in patients or mouse models. What is needed are new treatment methods and compositions that can repress the Adipogenic differentiation of FAPs and thus reduce muscle degeneration.

SUMMARY

Disclosed herein are methods relates to methods for treating, preventing, reducing, and/or inhibiting a muscular degenerative condition a muscular degenerative condition in a subject.

The details of one or more embodiments of the invention are set forth in the accompanying drawings and the description below. Other features, objects, and advantages of the invention will be apparent from the description and drawings, and from the claims.

In some aspects, disclosed herein are methods of treating, preventing, reducing, ameliorating, and/or inhibiting a muscular degenerative condition in a subject, said method comprising: administering to the subject an effective amount of a therapeutic agent that inhibits accumulation or adipogenesis of a fibro/adipogenic precursor (FAP) cell.

In one aspect disclosed herein are methods of treating, preventing, reducing, ameliorating, and/or inhibiting a muscular degenerative condition of any preceding aspect, wherein the muscular degenerative condition comprises a disease such as a muscular dystrophy, wherein the muscular dystrophy comprises duchenne muscular dystrophy (DMD), facioscapulohumeral muscular dystrophy (FSHD), or a limb-girdle muscular dystrophy (LGMD). In some embodiments, the limb-girdle muscular dystrophy is limb-girdle muscular dystrophy 2B.

Also disclosed herein are methods of treating, preventing, reducing, ameliorating, and/or inhibiting a muscular degenerative condition a muscular degenerative condition of any preceding aspect, wherein the muscular degenerative condition comprises age-related muscle weakness, muscular degeneration due to physical injury, disuse atrophy. In some embodiments, the physical injury comprises leg injury, ankle injury, hand injury, elbow injury, rotator cuff injury of the shoulder, or rotator cuff injury of the hip. In some embodiments, the limb-girdle muscular dystrophy is limb-girdle muscular dystrophy 2B. the age-related muscle weakness is sarcopenia.

In some embodiments, the subject is a human.

Also disclosed are methods of treating, preventing, reducing, ameliorating, and/or inhibiting a muscular degenerative condition of any preceding aspect, wherein the therapeutic agent an Annexin A2 (AnxA2) inhibitor, a matrix metalloproteinase (MMP) inhibitor, or a Toll-like receptor (TLR) signaling inhibitor (such as, for example, TLR-4), or a combination thereof (such as, for example, a small molecule, an RNA interference (RNAi) modulator, or an antibody or a functionally fragment thereof that inhibits AnxA2, MMP, and/or TLR-4). In some embodiments, the therapeutic agent comprises a small molecule AnxA2 inhibitor such as 1,2,4-triazoles; a small molecule MMP inhibitor (such as batimastat) and anti-MMP14 antibodies or fragments thereof, small molecule anti-histamines such as promethazine; a small molecule inhibitor of TLR signaling (such as, for example, Pepinh-MYD, TAK-242, Candesartan, Valsartan, Fluvastatin, Simvastatin, Atorvastatin, and/or ST2825); a small molecule matrix metalloproteinase (MMP)-14 inhibitor (such as, for example marimastat) or anti-MMP14 antibody; a glycogen synthase kinase 3 inhibitor (such as, for example, LY2090314); a histone deacetylase (HDAC) inhibitor (such as, for example, trichostatin A or or givinostat); a histamine inhibitor, (such as, for example promethazine); or an immunosuppressant (such as, for example, azathioprine).

In some embodiments, the method further comprises administering to the subject one or more anti-inflammatory agents.

DESCRIPTION OF DRAWINGS

FIGS. 1A, 1B, 1C, 1D, 1E, 1F, 1G, 1H, 1I, 1J, and 1K show adipogenic replacement of muscle correlates with disease severity in dysferlinopathic patients and mice. Mild, moderate and severely dystrophic LGMD2B patient and non-dystrophic control muscle cross-section stained with (1A) Oil Red O or for (1B) Perilipin-1 protein. FIG. 1C shows confocal images of LGMD2B patient muscle sections showing that perilipin-1 marked lipid deposits (red) accumulate outside the boundaries of laminin-marked myofiber borders (green). Scale bar=20 μm. FIG. 1D shows 12Mo B6A/J TA, gastrocnemius, quadriceps and psoas muscles stained for perilipin-1. Scale Bar=100 μm. Quantification (mean±SD) of (1E) myofiber central nucleation and (1F) perilipin-1 area across 12Mo B6A/J muscles. Statistical comparisons performed via t-test between adjacent groups, n=4 muscles/group. Quantification (Mean±SD) of (1G) myofiber central nucleation and (1H) perilipin-1 area from B6A/J gastrocnemius with advancing age/pathology, n=4 mice/group. Statistical comparisons performed via ANOVA with Holm-Sidak multiple comparisons test for all means with that of 12Mo WT, *p<0.05 p<0.01, *p<0.001. FIGS. 1I Oil Red O and (1J) Perilipin-1 labelling of gastrocnemius from 6, 12 and 18Mo B6A/J and 12Mo WT. Scale Bar=100 μm. FIG. 1K shows confocal image of gastrocnemius muscle sections showing that perilipin-1 marked lipid deposits (red) localize outside the boundaries of laminin-marked myofiber borders (green) in 12Mo B6A/J. Scale Bar=20 μm.

FIGS. 2A, 2B, 2C, and 2D show muscle histopathology and extracellular lipid deposition increase with clinical severity. FIG. 2A shows hematoxylin and eosin staining of LGMD2B biopsies demonstrating increased muscle pathology with increasing clinical severity. FIG. 2B shows perilipin-1 labelling from FIG. 1B, co-stained with wheat germ agglutinin to delineate myofiber membranes and demonstrate the extracellular lipid formation in LGMD2B patient muscle. FIG. 2C shows hematoxylin and eosin staining of B6A/J gastrocnemius demonstrating increased muscle pathology with increasing age. FIG. 2D shows perilipin-1 labelling from FIG. 1J, co-stained with wheat germ agglutinin to delineate myofiber membranes and demonstrate the extracellular lipid formation in B6A/J gastrocnemius with advancing age. Scales=100 μm FIGS. 3A, 3B, 3C, 3D, 3E, 3F, 3G, 3H, 3I, 3J, and 3K show FAP accumulation and differentiation dictates the extent of adipogenic replacement of dysferlin-deficient muscle. PDGFRα staining of FAPs in (3A) mild, moderate and severe LGMD2B patient and non-dystrophic control muscle cross sections; (3B) muscles with increasing pathology from 12Mo B6A/J and (3C) gastrocnemius muscle cross sections from 6, 12 and 18Mo B6A/J and 12Mo WT control. Scale Bar=20 μm. Quantification (mean±SD) of muscle area labeled with PDGFRα in (3D) human and mouse muscle with (3E) increasing pathology and (3F) increasing age. n=4 mice/group. Statistical comparisons performed via ANOVA with Holm-Sidak multiple comparisons test for all means with 12Mo TA or 12Mo WT respectively, *p<0.05, p<0.01, *p<0.001. FIG. 3G shows gastrocnemius muscle cross-section of 12Mo B6A/J co-labeled for PDGFRα and Perilipin-1. Scale Bar=50 μm. FIG. 3H shows Oil Red O staining of primary cell suspension isolated from hindlimb muscle of 6Mo B6A/J prior to (uninduced) or following (induced) induction for adipogenic differentiation. Scale Bar=200 μm. Inset shows a zoomed image of the box drawn in (3H). Oil Red O staining of sorted cells (3I) lacking or (3J) expressing PDGFRα at their cell surface. Scale Bar=200 μm. FIG. 3K shows FACS scatter plots showing cell surface labeling of PDGFRα in primary cell suspension prepared from mouse hindlimb muscle. The regions drawn mark the cells that express or lack cell surface PDGFRα expression.

FIG. 4A shows perilipin-1 staining of tibialis anterior, gastrocnemius, quadriceps and psoas of 12Mo WT mice shows the absence of extracellular lipid across all muscles. FIG. 4B shows PDGFRα staining from 12Mo WT muscles shows only the presence of muscle resident FAPs (individual cells at the junction of myofibers). Scales=50 μm.

FIGS. 5A, 5B, and 5C show notexin causes lipid deposition at the site of injury in dysferlin-deficient muscle. FIG. 5A shows schematic illustrating the single injury experimental procedure; a single 40 μl injection of notexin (5 μg/mL) was administered to the TA of B6A/J at 2 and 11Mo and 11Mo WT. Muscles were harvested 28 days later for analysis. FIG. 5B shows a schematic illustrating the repeat injury experimental procedure; B6A/J mice were injured by a series of 3 intramuscular notexin injections, each 14 days apart, from 10 to 11Mo. Muscles were harvested 28 days later for analysis. FIG. 5C shows Oil Red O staining of 12Mo B6A/J TA after a single notexin injury. Scale=200 μm. Shown are 2 regions approximately 900 μm apart, which illustrate both injured and uninjured regions of the muscle. Region 1 shows the injury site as marked by green tattoo dye (indicated by arrowheads), where centrally nucleated myofibers and Oil Red O-marked lipid are evident. Region 2 shows an uninjured area without tattoo dye, where only spontaneous regeneration and the absence of lipid can be seen.

FIG. 6: Injury induces FAP proliferation in older but not younger dysferlinopathic muscle. Images showing Perilipin-1 staining in cross-section of TA muscles from 2 and 12Mo in B6A/J or WT B16 mice following 4 weeks after (6A) a single or (6D) three rounds of notexin injury. Scale Bar=50 μm. Quantification (mean±SD) in TA muscle cross-section of (6B, 6E) total area and (6C, 6F) number of foci labeled with perilipin-1 after 4 weeks of (6B, 6C) single or (6E, 6F) 3-rounds of notexin injury. n=6 per group. Statistical comparisons performed via ANOVA with Holm-Sidak multiple comparisons test to compare all means with Uninjured 12Mo B6A/J, *p<0.05, p<0.01, *p<0.001, **P<0.0001. FIG. 1G shows images showing PDG1-Ra staining after single notexin injury of TA muscle from 12Mo WT, 2Mo and 12Mo B6A/J. Scale Bar=20 μm. FIG. 6**H shows Quantification (mean±SD) of PDGFRa-labeled area of the muscle after notexin injury, n=6 mice/group. Statistical comparisons between control and notexin injured performed via two-tailed t-test for each group. Comparisons between notexin injured muscles is by ANOVA with Holm-Sidak multiple comparisons test to compare all means with 12Mo WT, *p<0.05, *p<0.001, **P<0.0001.

FIGS. 7A, 7B, 7C, 7D, 7E, 7F, 7G, 7H, and 7I show extracellular accumulation of AnxA2 drives FAP accumulation in dysferlinopathic muscle. FIG. 7A shows AnxA2 staining in cross-sections from 6, 12 and 18Mo B6A/J and 12Mo WT mouse gastrocnemius muscle. Scale Bar=20 μm. FIG. 7B shows quantification (mean±SD) of total AnxA2-labeled area across the entire muscle cross section, n=4 mice/group. Statistical comparisons performed via ANOVA with Holm-Sidak multiple comparisons test to compare all means with 12Mo WT, *p<0.05, p<0.01, *P<0.001. FIG. 7C shows quantification (mean±SD) of (7D) co-localization between AnxA2 and PDGFRα in 12Mo B6A/J gastrocnemius, n=4 mice/group. Statistical comparisons performed via ANOVA with Holm-Sidak multiple comparisons test to compare all means with Uninjured 12Mo WT, *p<0.05, ***P<0.001. Confocal images from 12Mo B6A/J gastrocnemius co-labelled for (7E) AnxA2 and laminin, (7F) AnxA2 and F4/80 and (7G) PDGFRα and F4/80. Scale Bar=20 μm. (7H) Oil Red O and (7I) Perilipin-1 labelling of gastrocnemius cross sections from 12Mo B6A/J and A2-B6A/J. Scale Bar=50 μm.

FIGS. 8A, 8B, 8C, and 8D show Adipogenic conversion is blocked in A2-B6A/J muscle. FIG. 8A shows Oil Red O and (8B) Perilipin-1 staining of quadriceps sections from 24Mo B6A/J and A2-B6A/J. Scales=100 μm. FIG. 8C shows Oil Red O staining of B6A/J and A2-B6A/J FAPs after adipogenic induction. Scale=50 μm. FIG. 8D shows quantification of induced adipogenesis from 20,000 FAPs isolated from 24Mo B6A/J and A2-B6A/J. Data presented as mean SD.

FIGS. 9A, 9B, 9C, 9D, 9E, 9F, and 9G show that presence of AnxA2 is required for adipogenic conversion of dysferlinopathic muscle. FIG. 9A shows F4/80 staining of gastrocnemius of 12Mo WT, B6A/J and A2-B6A/J. Scale Bar=20 μm. Quantification (Mean±SD) of (9B) F4/80 labeled area, (9C) myofiber central nucleation, (9D) Perlipin-1 labeled area and (9E) PDGFRα labeled area from 12Mo WT, B6A/J and A2-B6A/J, n=4/genotype. Statistical comparisons performed via ANOVA with Holm-Sidak multiple comparisons test to compare all means, *p<0.05, p<0.01, *p<0.001. FIG. 9F shows quantification (mean±SD) of (G) PDGFRa-labeled area in 6, 12 and 24Mo A2-B6A/J gastrocnemius (Scale Bar=20 μm) shown in comparison to B6A/J (as presented in FIG. 2F), n=3 mice/group. Statistical comparisons performed by two-tailed t-test between B6A/J and A2-B6A/J at each timepoint, *p<0.05, **p<0.01.

FIGS. 10A, 10B, 10C, 10D, 10E, 10F, 10G, 10H, 10I, and 10J show that AnxA2 drives FAP adipogenesis and injury-triggered lipid formation in dysferlinopathic muscle. FIG. 10 shows Oil Red O staining and FIG. 10B shows quantification of spontaneous adipogenesis of 20,000 FAPs each, isolated from 12Mo WT, B6A/J and A2-B6A/J after 10 days in culture, n=3 replicates/genotype. Scale Bar=50 μm. FIG. 10C shows Oil Red O staining and FIG. 10D shows quantification (normalized to 20,000 FAPs) of spontaneous adipogenesis from a 1:1 mixed culture of 24Mo B6A/J FAPs (10,000 cells) with niche cells (10,000 cells) from either 24Mo B6A/J or A2-B6A/J. Scale Bar=50 μm. FIG. 10E shows Oil Red O staining and FIG. 10F shows quantification of spontaneous adipogenesis of 20,000 24Mo B6A/J FAPs left untreated or treated with 100 nM recombinant AnxA2. Scale bar=50 μm. FIG. 10G shows Perilipin-1 staining from 10Mo A2-B6A/J TA muscles 28 d after single notexin injury with (NTX+AnxA2) or without (NTX) co-administration of 10 μg recombinant AnxA2. Scale Bar=100 μm. FIG. 10H shows quantification of total perilipin-1 area after injury. FIG. 10I shows PDGFRα staining from 10Mo A2-B6A/J TA muscles 28 d after single notexin injury and administration of 10 μg recombinant AnxA2 compared to notexin injury alone. Scale Bar=20 μm. FIG. 10J shows quantification of total PDGFRα area after injury. All data presented as Mean±SD, average Oil Red area compared across genotypes by ANOVA with Holm-Sidak multiple comparisons test, all other data compared via two-tailed t-test, *p<0.05 ***p<0.001.

FIGS. 11A, 11B, 11C, 11D, 11E, and 11F show that Batimastat blocks FAP adipogenesis and reduces adipogenic loss of dysferlinopathic muscle. FIG. 11A shows Oil Red O staining and FIG. 11B shows quantification (normalized to 20,000 FAPs) of spontaneous adipogenesis from 40,000 FAPs each, isolated from 12Mo B6A/J, after 10 days in culture (n=3 replicates/group). Cells were treated with 10 μM batimastat starting day 3 in culture. Scale Bar=50 μm. FIG. 11C shows Perilipin-1 staining of 14Mo gastrocnemius muscle sections after 10 weeks of batimastat treatment. Scale Bar=100 μm. FIG. 11D shows quantification of perilipin-1 stained area in gastrocnemius muscle, n=3 muscles/group. FIG. 11E shows Perilipin-1 staining of TA muscles from 14Mo B6A/J mice after 3 successive notexin injuries while being treated (or left untreated) with batimastat. Scale Bar=100 μm. FIG. 11F shows quantification of injury-triggered lipid formation in notexin injured TA muscles corresponding to panel 11E, n=6 muscles/group. All quantifications shown are Mean±SD, and statistical comparisons were performed via two-tailed t-test, *p<0.05, ***P<0.001.

FIGS. 12A, 12B, 12C, 12D, 12E, 12F, 12G, 12H, and 12I show that Batimastat does not alter accumulation of FAPs or fibrotic deposition. FIG. 12A shows PDGFRα labelling and FIG. 12B shows quantification of PDGFRα area and (12C) myofiber central nucleation from 14Mo gastrocnemius sections following 10 weeks of batimastat treatment. Scale=20 μm. FIG. 12D shows PDGFRα labelling and FIG. 12E shows quantification of PDGFRα area from 14Mo TA sections after 3 repeat notexin injuries and batimastat treatment. Scale=20 μm. FIG. 12F shows Masson's trichrome staining and FIG. 12G shows quantification of fibrosis from 14Mo gastrocnemius sections following 10 weeks of batimastat treatment. Scale=100 μm. FIG. 12H shows Masson's trichrome staining and FIG. 12I shows quantification of fibrosis area from 14Mo TA sections after 3 repeat notexin injuries and batimastat treatment. Scale=100 μm. All data displayed as mean±SD.

FIGS. 13A, 13B, 13C, and 13D show that FAPs control the onset and severity of disease in LGMD2B. FIG. 13A shows healthy and/or pre-symptomatic LGMD2B muscle contains resident FAPs. FIG. 13B shows that after myofiber injury, inflammatory cells invade and trigger FAP proliferation. Successful regeneration involves a switch between pro-inflammatory and pro-regenerative signaling, causing the removal of inflammatory cells and FAPs. FIG. 13C shows that in symptomatic LGMD2B muscle there is a gradual accumulation of extracellular AnxA2, which prolongs the pro-inflammatory environment, causing excessive FAP proliferation. This cellular niche becomes pro-adipogenic over time, allowing for differentiation of FAPs and the adipogenic conversion of muscle. FIG. 13D shows blocking aberrant signaling due to AnxA2 buildup blocks FAP accumulation and thus preventing adipogenic loss of dysferlinopathic muscle. Similarly, use of a MMP-14 inhibitor (Batimastat) inhibits FAP adipogenesis offering a potential drug-based therapy to prevent adipogenic loss of dysferlinopathic muscle.

FIGS. 14A, 14B, 14C, 14D, 14E, and 14F show a summary of FACS gating to enrich for FAPs. FIG. 14A shows cells were first gated on size by Forward Scatter (FSC) by Side Scatter (SSC) to exclude dead cells and debris. FIG. 14B shows singlets were selected by gating on Forward Scatter (FSC) by the trigger pulse width. FIG. 14C shows that FAPs were identified using anti-PDGFRα conjugated to APC and FITC cell autofluorescence. Positive staining was confirmed by the absence of this APC-labelled population in (14D) unstained and (14E) isotype controls. FIG. 14F shows PDGFRα-labelled FAPs made up 13% of the total cell suspension obtained from 12Mo B6A/J muscle. Cells negative for anti-PDGFRα were also collected to serve as controls for in vitro experiments.

DETAILED DESCRIPTION

Figures 4A, 4B:
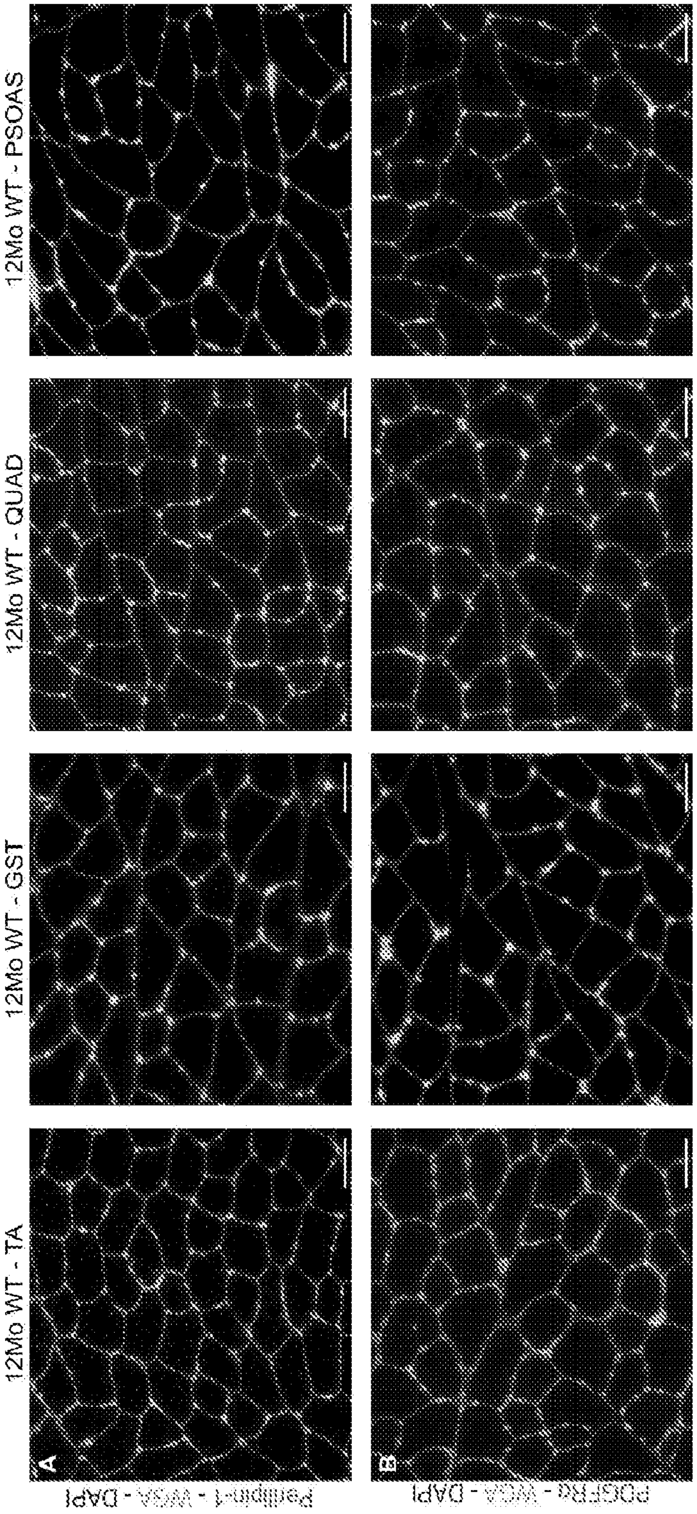
FIGS. 4A and 4B show extracellular lipid formation and FAP accumulation is absent in WT muscle.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

In the present invention, "specific" means a condition where one of the molecules involved in specific binding does not show any significant binding to molecules other than a single or a number of binding partner molecules. Furthermore. "specific" is also used when an antigen-binding domain is specific to a particular epitope among multiple epitopes contained in an antigen. When an epitope bound by an antigen-binding domain is contained in multiple different antigens, antigen-binding molecules containing the antigen-binding domain can bind to various antigens that have the epitope.

The term "subject" is defined herein to include animals such as mammals, including, but not limited to, primates (e.g., humans and nonhuman primates), cows, sheep, goats, horses, dogs, cats, rabbits, rats, mice and the like. In some embodiments, the subject is a human.

A "control" is an alternative subject or sample used in an experiment for comparison purposes. A control can be "positive" or "negative."

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain antigen binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

The fragments, whether attached to other sequences or not, include insertions, deletions, substitutions, or other selected modifications of particular regions or specific amino acids residues, provided the activity of the fragment is not significantly altered or impaired compared to the nonmodified antigen or the fragment thereof. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. *Nucl. Acids Res.* 10:6487-500 (1982).

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

"Polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule.

"Peptide," "protein," and "polypeptide" are used interchangeably to refer to a natural or synthetic molecule comprising two or more amino acids linked by the carboxyl group of one amino acid to the alpha amino group of another. The amino acids may be natural or synthetic, and can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" or "amino acid sequence" are an alphabetical representation of a polypeptide molecule.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of a muscular disease), during early onset (e.g., upon initial signs and symptoms of a muscular disease), or after an established development of muscular disease. Prophylactic administration can occur for several days to years prior to the manifestation of symptoms of a muscular disease.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Pharmacologically active", "functionally active" (or simply "active"), as in a "functionally active" derivative or analog, can refer to a derivative or analog (e.g., a salt, ester, amide, conjugate, metabolite, isomer, fragment, etc.) having the same type of pharmacological activity as the parent compound (e.g., an antibody) and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a chronic muscle disease developed after a physical injury). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

The term "small molecule" is used herein to refer to an organic, inorganic, or organometallic compound typically having a molecular weight of less than about 1000 daltons. Small molecule drugs of the invention encompass oligopeptides and other biomolecules having a molecular weight of less than about 1000 daltons.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

The term "muscular dystrophy" is a group of diseases that cause progressive weakness and loss of muscle mass. In muscular dystrophy, abnormal genes (mutations) interfere with the production of proteins needed to form healthy muscle. There are more than 30 other types of muscular dystrophy. In some embodiments, the muscular dystrophy comprises a muscular dystrophy, wherein the muscular dystrophy comprises a facioscapulohumeral muscular dystrophy (FSHD), duchenne type muscular dystrophy, a Becker muscular dystrophy, or a limb-girdle muscular dystrophy.

"Limb-girdle muscular dystrophy (LGMD)" refers to a diverse group of muscular diseases or disorders with many subtypes categorized by disease gene and inheritance. LGMD usually manifests in the proximal muscles around the hips and shoulders. It is the observed weakness and atrophy of the muscles connected to the limb girdles that has given this group of disorders its name. LGMD can be a Type 2 LGMD or a Type 2 LGMD. The Type 1 LGMD can be LGMD1A, LGMD1B, LGMD1C, LGMD1D, LGMD1E, or LGMD1F. They Type 2 LGMD can be LGMD2A, LGMD2B, LGMD2C, LGMD2D, LGMD2E, LGMD2F, LGMD2G, LGMD2H, LGMD2I, LGMD2J, LGMD2K, LGMD2L, LGMD2M, LGMD2N, LGMD2Q, LGMD2P, LGMD2Q, LGMD2R, LGMD2S, LGMD2T, LGMD2Q, LGMD2V, LGMD2W, LGMD2X, or LGMD2Y.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon Compositions and Methods Muscle injury triggers an acute myofiber repair response, failure of which causes myofiber death and resulting tissue infiltration by inflammatory cells. These cells clear the debris from the injury site and activate both satellite cell and FAP proliferation. A critical element in the regenerative process is transition of the pro-inflammatory cells to become pro-regenerative within 2-3 days after injury. This coincides with the apoptotic clearance of FAPs and with satellite cell fusion leading to myogenesis. Timely occurrence of the above cellular choreography between inflammatory, fibro/adipogenic, and satellite cells has been implicated in successful muscle regeneration. Consequently, disrupting inflammatory infiltration and FAP homeostasis impairs regeneration, resulting in fibrotic and adipogenic degeneration of injured muscle. This deficit has been demonstrated in the mouse model of Duchenne muscular dystrophy (mdx mice), where impaired FAP clearance results in muscle loss and fibrosis. Facilitating apoptotic clearance of FAPs reduces muscle loss and improves mdx muscle function in vivo.

It has also been shown that affected muscles of dysferlinopathic patients and mouse model show adipogenic replacement. Unlike the myofiber repair deficit and inflammation, adipogenic replacement is observed only in symptomatic patient and mouse muscle. Further, eccentric exercise exacerbates this phenotype in patients, suggesting a link between myofiber injury and adipogenic replacement of LGMD2B muscle. Muscle damage and disease severity in LGMD2B patients correlate with increased expression of another membrane repair protein Annexin A2 (AnxA2). Moreover, dysferlin deficient mice lacking AnxA2 have reduced myofiber repair ability, but are surprisingly protected from adipogenic myofiber loss. This indicates that loss of AnxA2 disrupts the link between injury and adipogenic replacement of dysferlin deficient myofibers.

Disclosed herein is the effect of dysferlin loss on the homeostasis of muscle-resident FAPs. By using dysferlinopathic patient and mouse models, it is shown that FAP accumulation and their adipogenic differentiation are key contributors to this muscular dystrophy. Importantly, the presence of extracellular AnxA2 promotes FAP proliferation and adipogenic differentiation, and the loss of AnxA2 or pharmacologically inhibiting FAP adipogenesis significantly ameliorates the dysferlin-deficient muscle pathology. The present disclosure shows FAPs and their adipogenic differentiation as a major contributor to dysferlin-deficient muscle loss, and shows FAP as a novel therapeutic target for treating, preventing, reducing, and/or inhibiting a muscular degenerative condition LGMD2B. Accordingly, disclosed herein is are methods of treating, preventing, reducing, and/or inhibiting a muscular degenerative condition (such as, for example, a muscle degenerative condition resulting from a disease or physical injury) in a subject, said method comprising: administering an effective amount of a therapeutic agent that inhibits accumulation or adipogenesis of a fibro/adipogenic precursor (FAP) cell.

It is understood and herein contemplated that muscular degenerative conditions can arise from genetic or infectious disease as well as physical injury, disuse atrophy, and/or age-related muscle weakness (such as, for example, sarcopenia). Thus, disclosed herein are methods of treating, preventing, reducing, and/or inhibiting a muscular degenerative condition a muscular degenerative condition wherein the muscular degenerative condition is the results of a physical injury. In some embodiments, the physical injury that causes the muscular disease comprises leg injury, ankle injury, hand injury, elbow injury, rotator cuff injury of the shoulder, or rotator cuff injury of the hip. As the timing of a physical injury can often not be predicted, it should be understood the disclosed methods of treating, preventing, reducing, and/or inhibiting a muscular degenerative condition can be used following the physical injury, prior to or following the onset of the muscular disease, to treat, prevent, inhibit, and/or reduce the muscular disease. Where, physical injury is due to a medical procedure, the disclosed methods can be performed any time prior to the onset of the muscular degenerative condition including prior to the cause of the injury. In one aspect, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to injury; concurrently with the injury; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days after injury, but prior to onset of any symptoms of a muscular degenerative condition.

In some embodiments, the muscular degenerative condition comprises a muscular dystrophy, which is a group of diseases that cause progressive weakness and loss of muscle mass. There are more than 30 other types of muscular dystrophy. Thus, disclosed herein are method of treating, preventing, reducing, and/or inhibiting a muscular degenerative condition wherein the muscular degenerative condition comprises a muscular dystrophy comprising, for example, duchenne type muscular dystrophy, facioscapulohumeral muscular dystrophy (FSHD), or a limb-girdle muscular dystrophy (LGMD). LGMD refers to a diverse group of muscular diseases or disorders with many subtypes categorized by disease gene and inheritance. Accordingly, in some embodiments disclosed herein are method of treating, preventing, reducing, and/or inhibiting a muscular degenerative condition, wherein the muscular degenerative condition comprises LGMD and wherein the LGMD can be of any subtypes including LGMD1A, LGMD1B, LGMD1C, LGMD1D, LGMD1E, LGMD1F, LGMD2A, LGMD2B, LGMD2C, LGMD2D, LGMD2E, LGMD2F, LGMD2G, LGMD2H, LGMD2I, LGMD2J, LGMD2K, LGMD2L, LGMD2M, LGMD2N, LGMD2O, LGMD2P, LGMD2Q, LGMD2R, LGMD2S, LGMD2T, LGMD2U, LGMD2V, LGMD2W, LGMD2X, or LGMD2Y. In some embodiments, the LGMD is LGMD2B.

In some aspects, it is understood and herein contemplated diseases that cause a muscular degenerative condition can be hereditary. Thus, the disclosed methods of treating, preventing, reducing, ameliorating, and/or inhibiting a muscular degenerative condition can be applied to a subject already afflicted with the muscular degenerative condition but prior to the onset of any physical symptoms. In some aspects, the disclosed methods of treating, preventing, reducing, ameliorating, and/or inhibiting a muscular degenerative condition (due to disease, aging, physical injury, or atrophy) can be applied to the subject after onset of physical symptoms. Thus, the methods are not preventing the degenerative condition as much as inhibiting progression or reducing the existing degeneration. Accordingly, disclosed herein are treating, preventing, reducing, ameliorating, and/or inhibiting a muscular degenerative condition; wherein the treatment commences after the onset of the condition and after symptoms are observable.

As the disclosed methods relate to addressing the muscular degenerative condition and not any underlying injury or disease (genetic or infectious), it is understood and herein contemplated that the disclosed treatments can be administered to the subject at a rate and for a duration appropriate for treating the muscular degeneration, including, but not limited to the inhibition of the progress of any existing muscular degeneration; reduction in any existing muscular degeneration; and/or the inhibition, reduction, and/or prevention of any future muscular degeneration. Thus, in one aspect, disclosed herein are methods of treating, preventing, reducing, and/or inhibiting a muscular degenerative condition, wherein the treatment is applied at a rate of 1, 2, 3, 4, 5, 6, 7, 8, 9, 10, 11, 12 or more times per day, 1, 2, 3, 4, 5, 6, or 7 times per week, 1, 2, 3, 4, 5, 6, 7, 8, 9, 10, 11, 12, 13, 14, 15, 16 or more times per month, 1, 2, 3, 4, 5, 6, 7, 8, 9, 10, 11, 12, 13, 14, 15, 16, 17, 18, 19, 20, 21, 22, 23, 24 or more times per year. In some aspect, the treatment can be applied a single time, twice, 3, 4, 5, 6, 7, 8, 9, 10, 11, 12, 13, 14, 15, 16, 17 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more times to the subject of a period of 1, 2, 3, 4, 5, 6, 7, 8, 9, 10, 11, 12, 13, 14, 21, 30, 31, 36, 45, 60, 75, 90 days, 3, 4, 5, 6, 7, 8, 9, 10, 11, 12, 16, 18, 24 months, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more years. In one aspect, the treatment is administered at the appropriate rate as determined by a physician for the remaining life of the subject.

In some embodiments, the therapeutic agent used in the disclosed methods of treating, preventing, reducing, and/or inhibiting a muscular degenerative condition comprises an Annexin A2 inhibitor, a matrix metalloproteinase (MMP) inhibitor, or a Toll-like receptor (TLR)-4 inhibitor, HDAC inhibitor, MMP-14 inhibitor, immunosuppressant, antihistamine, or a combination thereof. In some embodiments, the therapeutic agent comprises an Annexin A2 inhibitor. In some embodiments, the therapeutic agent comprises an MMP inhibitor. In some embodiments, the therapeutic agent comprises a TLR-4 inhibitor. In some embodiments, the therapeutic agent combination of any of an Annexin A2 inhibitor, an MMP inhibitor, and a TLR-4 inhibitor. In one aspect, it is understood and herein contemplated that the inhibitor of Annexin A2, MMP, and/or TLR-4 can comprise modulators of downstream effectors of the signaling pathway for Annexin A2, MMP, and/or TLR-4.

The Annexin A2 inhibitor can include any one or more agents which upon administration to a subject, can inhibit Annexin A2. The Annexin A2 inhibitor can directly affect Annexin A2, for example, by binding to the Annexin A2 protein or preventing the transcription or translation of an Annexin A2 gene. Alternatively, the Annexin A2 inhibitor can inhibit one or more other factors (e.g., one or more genes, proteins, mRNA) involved in the Annexin A2 pathway. In some embodiments, the Annexin A2 inhibitor comprises a small molecule, an interference RNA, or an antibody or a functionally fragment thereof. To avoid potential side effects from targeting the Annexin A2 pathway, the Annexin A2 inhibitor can target modulators downstream of the Annexin A2 signaling pathway or extracellular annexin signaling.

In some embodiments, the Annexin A2 inhibitor comprise a small molecule. In some embodiments, the small molecule comprises an AnxA2 tetramer inhibitors (A2ti). In some embodiments, the small molecule is 2-[4-(2-ethylphenyl)-5-o-tolyloxymethyl-4H-[1,2,4]triazol-3-ylsulfanyl]acetamide. In some embodiments, the small molecule is 2-(4-phenyl-5-o-tolyloxymethyl-4H-[1,2,4]triazol-3-ylsulfanyl)acetamide.

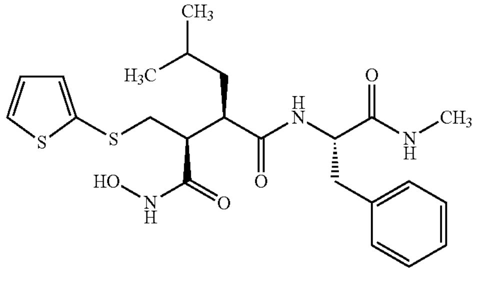 [SMILES: CNC(=O)[C@H](Cc1ccccc1)NC(=O)[C@H](CC(C)C)[C@H](CSc1cccs1)C(=O)NO]

In some embodiments, the Annexin A2 inhibitor can comprise an RNA interference (RNAi) modulator. RNAi modulators can be used to silence the expression of a gene (also known as "gene knock-down"), as opposed to genetic disruption of the gene (also known as "gene knock out"). RNAi modulators include, but are not limited to, small interfering RNA (siRNA), short hairpin RNA (shRNA), micro RNA (miRNA), trans-acting small interfering RNA (tasiRNA), long non-coding RNA (lncRNA), Piwi-interacting RNA (piRNA), among others. In some embodiments, the Annexin A2 inhibitor can comprise a siRNA, a shRNA, or a combination thereof. In some embodiments, the Annexin A2 inhibitor can be a morpholino, peptide inhibitor, an epigenetic inhibitor of Annexin A2.

In some embodiments, the Annexin A2 inhibitor can be an antibody or a functionally fragment thereof. The term "antibodies" is used herein in a broad sense and includes both polyclonal 5 and monoclonal antibodies. As used herein, the term "antibody" encompasses, but is not limited to, whole immunoglobulin (i.e., an intact antibody) of any class. In addition to intact immunoglobulin molecules, also included in the term "antibodies" are fragments or polymers of those immunoglobulin molecules, and human or humanized versions of immunoglobulin molecules or fragments thereof. It should be understood that the "antibody" can be monoclonal antibodies, polyclonal antibodies, chimeric antibodies, bispecific antibodies (diabody), or tri-specific antibody (triabody).

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, and the like, including hybrid fragments. Thus, fragments of the antibodies that retain the ability to bind their specific antigens are provided. For example, fragments of antibodies which maintain Annexin A2 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual.* Cold Spring Harbor Publications, New York, (1988)).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

In a complete antibody, typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant (C(H)) domains. Each light chain has a variable domain at one end (V(L)) and a constant (C(L)) domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively. In some embodiments, the antibody is of IgG1 isotype. In some embodiments, the antibody is of IgG2 isotype. In some embodiments, the antibody is of IgG3 isotype. In some embodiments, the antibody is of IgG4 isotype. In some embodiments, the antibody is of IgM isotype. In some embodiments, the antibody is of IgA isotype.

In some embodiments, the therapeutic agent comprises a matrix metalloproteinase (MMP) inhibitor. In some embodiments, the MMP inhibitor comprises a small molecule, an RNAi modulator, or an antibody or a functionally fragment thereof.

In some embodiments, the MMP inhibitor is a small molecule. The MMP inhibitor is selected from the group of consisting of MMP-1 inhibitor, MMP-2 inhibitor, MMP-3 inhibitor, MMP-4 inhibitor, MMP-7 inhibitor, MMP-8 inhibitor, MMP-9 inhibitor, MMP-10 inhibitor, MMP-11 inhibitor, MMP-12 inhibitor, MMP-13 inhibitor, MMP-14 inhibitor, MMP-15 inhibitor, MMP-16 inhibitor, MMP-17 inhibitor, MMP-18 inhibitor, MMP-19 inhibitor, MMP-20 inhibitor, MMP-21 inhibitor, MMP-23 inhibitor, MMP-24, inhibitor MMP-25 inhibitor, MMP-27 inhibitor, and MMP28 inhibitor. In some embodiments, the small molecule comprises an MMP-14 inhibitor. In some embodiments, the small molecule MMP inhibitor is batimastat. The structure of batimastat is shown below:

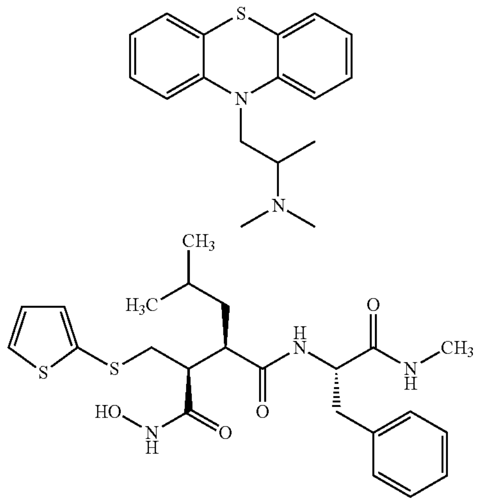

In some embodiments, the MMP inhibitor can comprise an RNA interference (RNAi) modulator. RNAi modulators include, but are not limited to, small interfering RNA (siRNA), short hairpin RNA (shRNA), micro RNA (miRNA), trans-acting small interfering RNA (tasiRNA), long non-coding RNA (lncRNA), Piwi-interacting RNA (piRNA), among others. In some embodiments, the MMP inhibitor can comprise a siRNA, a shRNA, or a combination thereof.

In some embodiments, the MMP inhibitor can be an antibody or a functionally fragment thereof. In some embodiments, the antibody is of IgG1 isotype. In some embodiments, the antibody is of IgG2 isotype. In some embodiments, the antibody is of IgG3 isotype. In some embodiments, the antibody is of IgG4 isotype. In some embodiments, the antibody is of IgM isotype. In some embodiments, the antibody is of IgA isotype.

In some embodiment, the therapeutic agent comprises a TLR-4 inhibitor. The TLR-4 inhibitor can include any one or more agents which upon administration to a subject, can inhibit TLR-4. The TLR-4 inhibitor can directly inhibit TLR-4, for example, by binding to the TLR-4 protein or preventing the transcription or translation of a TLR-4 gene. Alternatively, the TLR-4 inhibitor can inhibit one or more other factors (e.g., one or more genes, proteins, mRNA) involved in the TLR-4 pathway.

In some embodiments, the TLR-4 inhibitor comprises a small molecule, an RNAi modulator, or an antibody or a functionally fragment thereof. In some embodiments, the small molecule is selected from the group consisting of Pepinh-MYD, TAK-242, Candesartan, Valsartan, Fluvastatin, Simvastatin, or Atorvastatin. In some embodiments, the small molecule is TAK-242. The structure of TAK-242 is shown below:

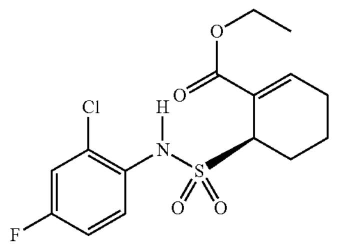 [SMILES: CCOC(=O)C1=CCCC[C@H]1S(=O)(=O)Nc1ccc(F)cc1Cl]

In some embodiments, the small molecule is Candesartan. The structure of Candesartan is shown below:

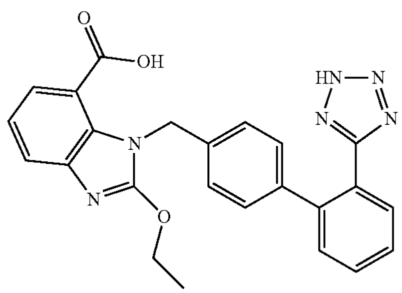 [SMILES: CCOc1nc2cccc(C(=O)O)c2n1Cc1ccc(-c2ccccc2-c2nn[nH]n2)cc1]

In some embodiments, the small molecule is Valsartan. The structure of Valsartan is shown below:

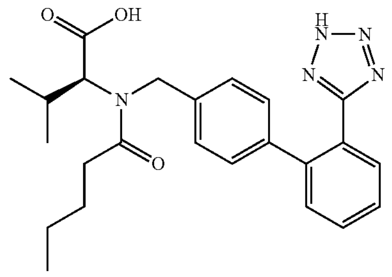 [SMILES: CCCCC(=O)N(Cc1ccc(-c2ccccc2-c2nn[nH]n2)cc1)[C@H](C(=O)O)C(C)C]

In some embodiments, the small molecule is Fluvastatin. The structure of Fluvastatin is shown below:

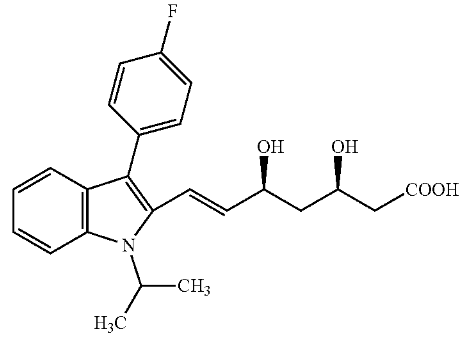 [SMILES: CC(C)n1c(/C=C/[C@@H](O)C[C@@H](O)CC(=O)O)c(-c2ccc(F)cc2)c2ccccc21]

In some embodiments, the small molecule inhibitor is Simvastatin. The structure of Simvastatin is shown below:

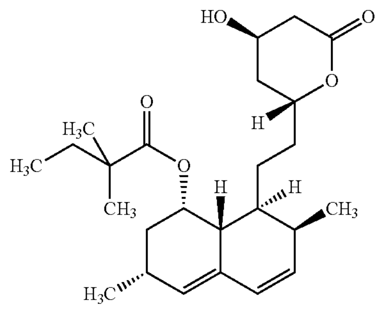 [SMILES: CCC(C)(C)C(=O)O[C@H]1C[C@@H](C)C=C2C=C[C@H](C)[C@H](CC[C@@H]3C[C@@H](O)CC(=O)O3)[C@H]21]

In some embodiments, the small molecule inhibitor is Atorvastatin. The structure of Atorvastatin is shown below:

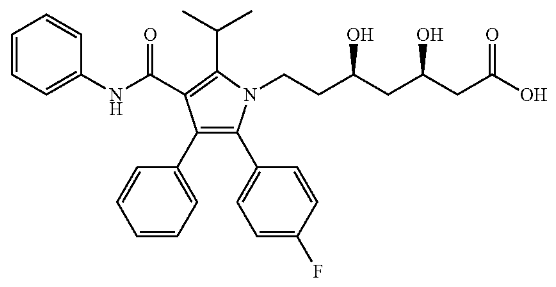 [SMILES: CC(C)c1c(C(=O)Nc2ccccc2)c(-c2ccccc2)c(-c2ccc(F)cc2)n1CC[C@@H](O)C[C@@H](O)CC(=O)O]

In some embodiments, the TLR-4 inhibitor can comprise an RNA interference (RNAi) modulator. RNAi modulators include, but are not limited to, small interfering RNA (siRNA), short hairpin RNA (shRNA), micro RNA (miRNA), trans-acting small interfering RNA (tasiRNA), long non-coding RNA (lncRNA), Piwi-interacting RNA (piRNA), among others. In some embodiments, the TLR-4 inhibitor can comprise a siRNA, a shRNA, or a combination thereof.

In some embodiments, the TLR-4 inhibitor can be an antibody or a functionally fragment thereof. In some embodiments, the antibody is of IgG1 isotype. In some embodiments, the antibody is of IgG2 isotype. In some embodiments, the antibody is of IgG3 isotype. In some embodiments, the antibody is of IgG4 isotype. In some embodiments, the antibody is of IgM isotype. In some embodiments, the antibody is of IgA isotype.

It should be understood that the TLR-4 inhibitor can be an inhibitor for one or more other factors (e.g., one or more genes, proteins, mRNA) involved in the TLR-4 pathway. MyD88 is an adaptor protein which dimerizes upon TLR-4 activation and transduces signaling downstream of TLR-4. Thus, the TLR-4 inhibitors disclosed herein also encompass inhibitors targeting MyD88. These MyD88 targeting inhibitors comprise small molecules inhibiting MyD88 dimerization (e.g., T6167923), or peptide inhibitors of MyD88 (e.g., Pepinh-MYD). In some embodiments, the MyD88 inhibitor comprises an antibody or a functional fragment thereof.

In some embodiments, the therapeutic agent comprises a platelet-derived growth factor receptor a (PDGFRa) inhibitor. In some embodiments, the PDGFRα inhibitor comprises imatinib, nilotinib, sunitinib. In some embodiments, the PDGFRα inhibitor is a morpholino which manipulates PDGFRα gene splicing.

In some embodiments, the therapeutic agent comprises a histone deacetylase inhibitor, wherein the histone deacetylase inhibitor comprises trichostatin A or givinostat.

In some embodiments, the therapeutic agent comprises a histamine inhibitor, wherein the histamine inhibitor comprises promethazine.

In some embodiments, the therapeutic agent comprises an immunosuppressant, wherein the immunosuppressant comprises azathioprine.

In some embodiments, the therapeutic agent comprises a small molecule matrix metalloproteinase (MMP)-14 inhibitor (such as, for example marimastat) or anti-MMP14 antibody.

In some embodiments, the therapeutic agent comprises a glycogen synthase kinase 3 inhibitor (such as, for example, LY2090314).

In some embodiments, the therapeutic agent comprises an IL-4 or IL-1β inhibitor.

In one aspect, it is understood and herein contemplated that the disclosed methods of treating a muscular degeneratinve disease, can, in addition to administering the disclosed Annexin A2, MMP, and/or Toll-like receptor (TLR)-4 inhibitors, further comprise administering to a subject with a muscular degenerative disease any treatment already known for the use in treatment of muscular degenerative diseases. For example, the methods can further comprise the administration of deflazacort, eteplirsen, golodirsen, glucocorticoids (such as, for example, prednisone and/or VBP15), angiotensin-converting enzyme (ACE) inhibitors and/or beta blockers.

As noted above, dosing frequency for the therapeutic agent (e.g. batimastat), or a pharmaceutically acceptable salt thereof, includes, but is not limited to, at least about once every three months, once every two months, once every month, once every three weeks, once every two weeks, or once a week. In some embodiments, the dosing frequency for the therapeutic agent, includes, but is not limited to, at last, about once every 14 days, once every 13 days, once every 12 days, once every 11 days, once every 10 days, once every 9 days, once every 8 days, once every 7 days, once every 6 days, once every 5 days, once every 4 days, once every 3 days, once every 2 days, or daily. In some embodiments, the interval between each administration is less than about a week, such as less than about any of 6, 5, 4, 3, 2, or 1 day. In some embodiments, the dosing frequency for the therapeutic agent includes, but is not limited to, at least once a day, twice a day, three times a day, or four times a day. In some embodiments, the interval between each administration is less than about 48 hours, 36 hours, 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is less than about 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is constant. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between a course of administration is no more than about a week.

It is understood and herein contemplated that the disclosed methods of treating, preventing, reducing, and/or inhibiting a muscular degenerative condition can be administered to any subject with a muscular degenerative condition including, but not limited to humans, dogs, cats, horses, cows, mice, rats, pigs, sheep, and non-human primates.

EXAMPLES

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Example 1: Muscle Adipogenesis Determines LGMD2B Onset and Severity

MRI and histological analyses have identified fatty replacement of muscle in symptomatic dysferlinopathic patients and mouse models. How this association relates to disease severity is examined by direct histological analysis of muscle sections from LGMD2B patients and mouse model. Muscle biopsies were obtained from LGMD2B patients who exhibited mild to severe clinical symptoms described in Table 1. As a first step, the neutral lipid stain Oil Red O were used to score the adipogenic status of muscle sections from these patients. While sections of healthy muscle showed little to no oil red staining, extensive staining was noted between the myofibers in symptomatic patient muscle sections, which increased with the severity of the patient's clinical symptoms and the extent of muscle loss (FIG. 1A, FIG. 2). To further examine if the adipogenic deposits were originating from within the myofibers, the localization of Perilipin-1, a protein that coats the adipocyte lipid droplets, was examined No perilipin-1 staining was detectable in healthy muscle, but patient muscles showed extensive perilipin-1 labeling, which increased with disease severity and localized exclusively in the extracellular matrix space between the myofibers (FIGS. 1B and 1C). Patient myofibers did not show internal perilipin-1 labeling even when they are adjacent to lipid deposits (FIG. 1C, FIG. 2), indicating extra-myofiber origin of these lipids.

ment of dysferlinopathic muscle. With the known proliferation of FAPs in the muscle interstitium following injury, and their adipogenic potential, it was examined the next if FAPs lead to adipogenic conversion of LGMD2B muscle. Using PDGFRα to label FAPs, control biopsies showed minimal interstitial PDGFRα staining, which was evident in LGMD2B patients and increased with worsening clinical severity (FIG. 3A, 3D). Analysis of mouse muscles showed a similar interstitial accumulation of PDGFRα in B6A/J, which correlates both to extent of disease severity across muscles at the same age (FIG. 3B, 3E), and to increasing disease severity due to age of the muscle (gastrocnemius) from 6 months onwards (FIG. 3C, 3F). This is a feature of the dysferlinopathic mice, and is not observed in the healthy, wild type (WT) mice (FIG. 4). PDGFRα-labeled FAP increase occurred concomitantly with the increase in central nucleation, but prior to adipogenic replacement of the myofibers (FIG. 3F compared to FIG. 1F). This observation shows that persistent myofiber injury and regeneration causes FAP accumulation. Subsequent adipogenic differentiation of these FAPs causes adipogenic replacement of the myofibers, as indicated by the formation of lipid deposits in extracellular matrix regions being enriched for PDGFRα-marked FAPs (FIG. 3G).

TABLE 1

Summary of LGMD2B patient biopsies included for analysis.

| Sample | Sex | Age at Diagnosis | Age at Biopsy | Mutations in DYSF | Clinical Symptoms |
|---|---|---|---|---|---|
| Mild | M | 19 | 21 | c.937 + 1G > A<br>c.5594delG | Mild weakness, difficulty running and climbing stairs. |
| Moderate | F | 15 | 35 | c.5528delG<br>c.6348dupA | Requires a cane for walking, unable to raise arms, needs help standing from floor. |
| Severe | M | 18 | 30 | c.2779delG<br>c.4410 + 13T > G | Severe weakness in both limbs, requires the use of a wheelchair. |
| Control 1 | M | — | 21 | — | — |
| Control 2 | M | — | 17 | — | — |
| Control 3 | M | — | 17 | — | — |

To independently assess the link between disease severity and the extent of adipogenic replacement of muscle, muscles from 12-month old dysferlin-deficient (B6A/J) mice were examined (FIG. 1D). Disease severity, as indicated by the extent of damage and regeneration (myofiber central nucleation) showed a progressive increase between muscles in the following order: TA, gastrocnemius, quadriceps, psoas (FIG. 1E). Labeling with perilipin-1 showed a parallel increase in lipid accumulation between the myofibers across these same muscles (FIG. 1D, 1F). Similarly, muscle (gastrocnemius) collected from mice with increasing age (6 to 18 months old) showed progressively increasing adipogenic replacement marked by increased labeling with either Oil Red O (FIG. 1I) or perilipin-1 (FIG. 1J). While increased perilipin-1 staining is detected starting 12 months (FIG. 1H), these muscles showed an increased central nucleation starting from 6 months (FIG. 1G), indicating that myofiber damage and regeneration precedes their later adipogenic replacement. Again, in the mouse muscle, perilipin-1 labeling was observed only in the extracellular matrix and not in adjacent myofibers (FIG. 1K), indicating that the lipid does not originate in muscle fibers, and instead is produced by muscle interstitial cells.

Example 2. FAPs Cause the Adipogenic Loss of Dysferlinopathic Muscle

The above results indicate the extent of muscle damage and regeneration preempts the degree of adipogenic replace- To directly assess the role of FAPs in adipogenic replacement of dysferlinopathic myofibers, a mixed primary cell suspension was obtained from hindlimb muscles of 6Mo B6A/J mice. Inducing cells with adipogenic media caused a proportion of cells to differentiate into oil red-labeled adipocytes, such that even when these adipocytes were found adjacent to myotubes, the myotubes themselves were not producing the lipids (FIG. 3H). This further supports that non-myogenic cells produce the adipogenic material that eventually replace myofibers. To establish the identity of these adipogenic cells, fluorescence-activated cell sorting was used to isolate PDGFRα-labeled (PDGFRα$^+$) FAPs and PDGFRα-unlabeled (PDGFRα) cells from a primary muscle cell suspension (FIG. 3K). Even upon adipogenic induction, no adipocyte formation was observed in PDGFRα$^-$ cells (FIG. 3I). However, PDGFRα$^+$ cells formed adipocytes spontaneously, which increased further upon adipogenic induction (FIG. 3J). These results identify FAPs as the muscle interstitial cells that contribute to the adipogenic loss of dysferlin-deficient muscle.

Example 3. Adipogenic Muscle Loss Depends on Age and Myofiber Injury

Above observations indicate that age, chronic injury, and poor repair of dysferlinopathic myofibers create a niche that promotes progressive interstitial FAP accumulation and subsequent differentiation into adipocytes. To test this, it was examined herein whether injury and age of the TA (a muscle that is minimally affected in B6A/J) can unmask the adipogenic potential of the FAPs and effect of tissue injury and age on this process. TA muscles from 3Mo and 12Mo B6A/J mice were injured by notexin and after allowing 4 weeks for myofibers to fully regenerate, the extent of adipogenic muscle replacement was scored and compared to the uninjured 12mo B6A/J TA (FIG. 5). The uninjured 12Mo, and the injured 3Mo B6A/J TAs both lack significant adipogenic replacement (assessed by perilipin-1 staining) (FIGS. 6A, 6B, and 6C). In contrast, the injured 12Mo B6A/J TA showed a substantially increased adipogenic foci and myofiber areas replaced by adipogenesis (FIGS. 6A, 6B, and 6C). This showed that increasing age increases injury-triggered adipogenic replacement of areas otherwise occupied by myofibers. This link is further strengthened by the observation that adipogenic replacement occurs at the site of notexin injection (marked by tattoo dye), while adjacent uninjured regions remained non-adipogenic (FIG. 5). These results establish muscle injury and age enhance adipogenic replacement of dysferlinopathic muscle.

To confirm that this post-injury lipid formation was due to the absence of dysferlin, TAs from 12Mo WT were injured, which showed no significant lipid formation after injury (FIGS. 6D, 6E, and 6F). Dysferlinopathic muscle undergoes repeat bouts of injury over the disease course, which leads to adipogenic replacement of the muscle. To show this, three consecutive injuries to the TA muscle were performed in dysferlinopathic mice, allowing two-week regeneration periods between the injuries (FIG. 5). This resulted in more adipogenic replacement of the TA muscle than in the single injured TA muscle (FIGS. 6D, 6E, and 6F), indicating that repeat rounds of myofiber injury and regeneration drive the adipogenic conversion of dysferlinopathic muscle. To examine if this injury-dependent adipogenic replacement was a consequence of increased FAP accumulation caused by the injuries, these muscles were examined for PDGFRα (FIG. 6G). Compared to uninjured B6A/J muscles and WT muscles, there was a significant increase in PDGFRα-labeled FAPs in injured B6A/J muscles (FIG. 6H). Injured 12Mo B6A/J muscle accumulates significantly more FAPs than both the 3Mo B6A/J and the 12Mo WT injured muscles, indicating that excessive FAP accumulation after injury is a feature of dysferlin-deficient muscle with advancing pathology, and underpins the adipogenic loss of these muscles.

Example 4. AnxA2 Links Muscle Injury to FAP Activation and Adipogenesis

The above link between FAP accumulation and adipogenic replacement of dysferlinopathic muscle indicates that accumulation and adipogenic differentiation of FAPs is responsible for the decline in dysferlinopathic muscle function, and reversing this can provide a therapy for LGMD2B. AnxA2 is a membrane repair protein that is elevated upon muscle injury and increases in LGMD2B patient muscle in a manner that correlates with disease severity. It has been shown that deletion of AnxA2 in dysferlinopathic muscle reduces adipogenic replacement and improves muscle function despite no improvement in myofiber repair. Thus, it was examined herein if AnxA2 contributes to FAP proliferation/adipogenic differentiation in dysferlinopathic muscle Immunostaining for AnxA2 showed that in dysferlinopathic mice AnxA2 level increases with disease severity and that this increase is in the level of AnxA2 in the interstitium (FIG. 7A, FIG. 7B, FIG. 7E). Co-labelling with PDGFRα showed that the FAPs are enriched in the regions with accumulation of AnxA2 (FIG. 7C, FIG. 7D). AnxA2 expression increases after muscle injury, and extracellular AnxA2 can activate inflammation via toll-like receptor 4 (TLR4). An investigation was thus performed to exam if the inflammatory cells are enriched at the sites of AnxA2 accumulation. F4/80 marked macrophages accumulated in interstitial regions enriched for AnxA2 (FIG. 7F), and are located adjacent to the PDGFRα-labeled FAPs (FIG. 7G). To analyze if AnxA2 accumulation is causally linked to adipogenic replacement via FAPs, adipogenic replacement and FAP accumulation was examined in mice lacking dysferlin and AnxA2 (A2-B6A/J). Oil Red O and perilipin-1 labeling both revealed significantly less adipogenic replacement of muscle in A2-B6A/J than B6A/J mice (FIG. 7H, FIG. 7I, FIG. 8 and quantified in FIG. 9D). This indicates that extracellular AnxA2 accumulation contributes to the pro-adipogenic niche as AnxA2 deletion arrests the adipogenic conversion of dysferlinopathic muscle.

As macrophages are enriched at sites of PDGFRα and AnxA2 accumulation, it was examined if the lack of extracellular AnxA2 works by inhibiting muscle inflammatory response. F4/80 staining of 12Mo gastrocnemius muscles showed that compared to the WT mice, both B6A/J and A2-B6A/J mice show a robust increase in macrophage infiltration (FIG. 9A, 9B). The extent of macrophage infiltration in these mouse muscles is in line with the extent of myofiber injury, indicated by the number of centrally nucleated myofibers in B6A/J and A2-B6A/J mice as compared to WT mice (FIG. 9C). In contrast to the higher injury and inflammation of A2-B6A/J muscle (as compared to the WT), FAP (PDGFRα) accumulation and lipid (perilipin-1) formation was comparable between the A2-B6A/J and WT muscle (FIG. 9D, 9E). This raises the possibility that the beneficial effect of the lack of AnxA2 may be by way of its effect on FAP proliferation and adipogenic differentiation. To examine the effect of AnxA2 on FAP accumulation and on preventing their adipogenic differentiation, FAP accumulation was quantified using PDGFRα labeling. While B6A/J mice showed increasing accumulation of FAPs with age, muscles in the A2-B6A/J mice showed fewer FAPs, and their numbers did not increase with age (FIG. 9F, 9G). This indicates that lack of AnxA2 prevents FAP accumulation, contributing to the suppression of adipogenic replacement of dysferlin-deficient muscle.

The contribution of AnxA2 to the adipogenic fate of the FAPs was next examined in dysferlin-deficient muscle. For this FAPs were isolated from 12Mo WT, B6A/J and A2-B6A/J muscle and their spontaneous adipogenesis in vitro was quantified. A small proportion of WT FAPs undergo spontaneous adipogenesis after 14 days in culture, but B6A/J FAPs show significantly higher rates of adipogenesis (FIG. 10A, 10B). The spontaneous adipogenesis of B6A/J FAPs indicates these cells are committed to adipogenesis prior to extraction, which can be caused by the pro-adipogenic niche in dysferlinopathic muscle. The lack of spontaneous adipogenesis in A2-B6A/J FAPs can be caused by the lack of a pro-adipogenic niche or restricted adipogenic potential of the FAPs in the absence of AnxA2 (FIG. 8). As adipogenic replacement of muscle is enhanced with age, the niche ($PDGFR\alpha^-$) and FAP ($PDGFR\alpha^+$) cells from 24Mo B6A/J and A2-B6A/J muscles were isolated to allow for the niche cells to reach their maximal potential. These FAP and niche cells were then mixed in a 1:1 ratio (20,000 cells total; 10,000 FAPs) from the same or different genetic background and their spontaneous adipogenesis was quantified as the extent of oil red staining/20,000 FAPs. Compared to the B6A/J niche, the A2-B6A/J niche restricted the spontaneous adipogenesis of B6A/J FAPs (FIGS. 10C, and 10D). Thus, absence of AnxA2 in the niche cells reduces the adipogenicity of the dysferlinopathic FAPs. To directly test if it is the AnxA2 or another factor secreted by the niche cells that influences FAP adipogenesis, a purified population of B6A/J FAPs (20,0000 FAPs) were treated with 100 nM AnxA2 and their spontaneous adipogenesis was quantified as the extent of oil red staining/20,000 FAPs. Compared to the AnxA2 untreated FAPs, treatment with purified AnxA2 alone caused a >2-fold increase in the spontaneous adipogenic differentiation of these dysferlinopathic FAPs (FIG. 10E, 10F).

Taken together, the above results show that AnxA2 produced by the B6A/J muscle niche cells can potentiate the adipogenic differentiation of B6A/J FAPs in vitro. To test if this was also true in vivo, the AnxA2-naïve A2-B6A/J mice were used for receiving notexin to injure their muscle with or without the addition of 10 μg purified AnxA2 at the site of injury. Presence of exogenous AnxA2 at the site of muscle regeneration in these otherwise AnxA2 deficient muscles resulted in increased accumulation of the PDGFR±FAPs as well as perilipin-1 labeled adipogenic deposits (FIGS. 10G, 10H, 10I, and 10J). This provides direct evidence supporting that extracellular AnxA2 is not only necessary, but also sufficient for driving FAP-mediated in vivo adipogenic conversion of the regenerating dysferlinopathic muscles.

Example 5. Blocking FAP Differentiation Arrests Adipogenic Muscle Loss

The data from the A2-B6A/J model shown above indicates that restricting the adipogenic conversion preserves the dysferlinopathic muscle and is thus a potential therapeutic target. To test this, and to independently confirm the benefit of inhibiting adipogenic differentiation of FAPs for dysferlinopathy, a drug was used to inhibit adipogenic differentiation of FAPs. Batimastat is small molecule drug that has previously been shown to restrict adipogenesis of both cultured adipogenic precursors and WT mouse FAPs. To test the ability of batimastat to prevent the spontaneous adipogenesis of B6A/J FAPs, 40,000 FAPs isolated from 12Mo B6A/J mice were treated with 10 μM batimastat starting from 3 days in culture. Using Oil Red O, the extent of adipogenic differentiation of these FAPs after 14 days in culture was quantified in vitro (FIG. 11A). It is shown that treatment with batimastat resulted in reduced spontaneous adipogenesis of the B6A/J FAPs (FIG. 11B).

Whether this effect of batimastat to repress FAP adipogenesis can improve muscle histopathology was tested in vivo. 12Mo B6A/J mice were treated for 10 weeks with batimastat (2 mg/kg i.p. 3× weekly). As B6A/J gastrocnemius muscle showed significant adipogenic replacement starting from the age of 12Mo (FIG. 11I), the extent of adipogenic loss in this muscle was assessed (FIG. 11C). Compared to the untreated mice, muscles from batimastat treated mice showed significantly reduced perilipin-1 labeled area (FIG. 11D). To determine if this reduction in adipogenic replacement was due to an effect on just FAP differentiation or also on FAP proliferation, FAP accumulation was quantified by PDGFRα labeling and no effect of batimastat treatment on FAP number was found (FIG. 12). Similarly, batimastat treatment of 12Mo B6A/J mice did not decrease the extent of myofiber central nucleation (FIG. 12). Thus, inhibition of adipogenesis by batimastat is not due to reduced FAP numbers or improved myofiber repair. To further confirm the ability of batimastat to prevent dysferlinopathic muscle from injury-triggered FAP adipogenesis, we employed the repeat notexin-induced TA injury approach which induces significant adipogenic replacement of the muscle (FIG. 6D and FIG. 6E). Compared to the untreated mice, TA muscles from batimastat treated mice showed a nearly 40% reduction in perilipin-1 positive area following repeat notexin injury (FIG. 11E and FIG. 11F). Again, this reduction was due to restriction of adipogenic differentiation of the FAPs and not due to an effect on their proliferation, as batimastat treatment did not reduce the FAP accumulation caused by repeat notexin injuries (FIG. 12). Given that FAP numbers are unaffected by batimastat treatment, it was examined whether these batimastat treatment causes cells to adopt a fibrogenic fate by blocking their adipogenic differentiation. However, no change in intra-muscular fibrosis was observed as a result of batimastat treatment in either the gastrocnemius or injured TA (FIG. 12). Taken together, the above results both confirm the essential nature of FAP adipogenesis for the adipogenic conversion of dysferlinopathic muscle, and highlight the potential of batimastat to arrest the progressive and even late stage adipogenic replacement of dysferlinopathic muscle.

Example 6: Discussion

Myofiber loss and the associated muscle weakness is a feature of many muscular dystrophies. Thus, in the search for innovative therapies, it is important to elucidate the cellular mechanisms that link the initial genetic defect to disease onset and progression. In LGMD2B, absence of dysferlin in myofibers inhibits sarcolemmal repair, disrupts proper calcium homeostasis at the t-tubules, and alters the response of innate immune cells. Restoration of dysferlin expression in myogenic cells and blockade of innate immune activation reduces pathology in dysferlin-deficient mice, indicating that both the myofiber and inflammatory cell specific deficits contribute to disease symptoms in dysferlinopathy. However, these deficits fail to explain the abrupt and late onset of disease in patients and the observation that adipogenic replacement is a feature of symptomatic dysferlinopathic muscle. The present disclosure shows evidence that disease onset and progression in dysferlinopathy is not driven solely by the myofiber and inflammatory cell-specific defects, but by creation of an extracellular niche resulting in proliferation and adipogenic differentiation of muscle-resident FAPs.

From early in the disease, the primary myofiber defects lead to persistent myofiber damage. AnxA2, a dysferlin interacting protein that accumulates at the injured membrane and aids in its repair is released at the site of plasma membrane injury. This AnxA2 released at the site of injured myofibers can trigger muscle inflammation, which in acute injury facilitates myofiber regeneration. However, in LGMD2B patients AnxA2 levels are chronically increased in a manner that correlates with disease severity. Given that AnxA2 expression is ubiquitous, AnxA2 can also be produced by myofibers or other cells present in the injured muscle, including the FAPs, endothelial and inflammatory cells. AnxA2 released chronically in the extracellular matrix of dysferlinopathic muscle creates a niche which favors increased proliferation and subsequently, adipogenic differentiation of FAPs (FIG. 13). Consistent with this understanding, AnxA2 is a critical component of the pro-adipogenic FAP niche in dysferlinopathic muscle, as deletion of AnxA2 both decreases extracellular matrix FAP accumulation and prevents their commitment to adipogenesis (FIG. 7 and FIG. 9). Presence of AnxA2 expressing niche cells in the muscle increases FAP adipogenesis and purified AnxA2 in regenerating muscle is capable of increasing FAP accumulation and adipogenesis in regenerating dysferlinopathic muscle (FIG. 10 and FIG. 11). These in vitro and in vivo analyses independently confirm an active role AnxA2 in the adipogenic conversion of dysferlinopathic muscle.

In addition to the direct action of AnxA2 on FAPs, it can also act indirectly via inflammatory or other cell types. In support of such a role of AnxA2, it is shown that dysferlinopathic muscle lacking AnxA2 show reduction in the extent of macrophage infiltration (FIG. 9). This can be due to the ability of AnxA2 to function as an agonist for innate immune response. It was shown that AnxA2 knockout in B6A/J mice down-regulates TLR4 signaling. Inhibiting TLR signaling by deletion of the central TLR adapter protein Myd88 reduces pathology in dysferlinopathic (A/J) mice. Innate immune signaling has been implicated in the dysferlinopathic symptoms, and dysferlin-deficient muscles show a greater abundance of pro-inflammatory as compared to pro-regenerative macrophages. Together, these can contribute to delayed/impaired myogenesis, further enabling FAP accumulation. Repeat rounds of myofiber injury, chronic inflammation, and FAP accumulation as the muscle ages sets up a feed-forward loop linking myofiber damage to the formation of a pro-adipogenic niche over time, which in turn contributes to myofiber damage (FIG. 12). In such a system adipogenic accumulation becomes the nucleating event that results in clinical onset, and an abrupt decline in muscle function in patients. Thus, while dysferlinopathy is driven by a myofiber specific deficit, it is the impaired cellular interactions between myofibers, inflammatory cells and FAPs that is causative for disease initiation and severity. This view of the disease opens up previously unrecognized avenues to intervene, as has been realized in DMD where inhibition of TGFβ-induced FAP accumulation reduces muscle fibrosis and leads to therapeutic benefits.

Use of mdx mice shows that aberrant FAP accumulation and differentiation drives disease pathogenesis in DMD. While these FAPs primarily exhibit fibrogenic fate via TGFβ signaling, in vitro they also exhibit adipogenic potential. Their adipogenic potential diminishes with age, advancing pathology and by the use of HDAC inhibitors. This contrasts with the in vivo increase in adipogenic fate of FAPs observed in dysferlinopathic mice. This difference between the dystrophin (mdx) and dysferlin (B6A/J) mouse models indicates spontaneous fibrogenic commitment of the mdx and adipogenic commitment of B6A/J FAPs. Inhibition of matrix metalloproteases (MMPs) is known to decrease the conversion of 3T3-L1 and primary rat preadipocytes into adipocytes. Analyses of the FAPs show that pharmacological inhibition of MMP-14 represses C/EBPδ and PPARγ in FAPs by way of cilial hedgehog signaling and this reduces the adipogenic fate of FAPs. Adipogenesis of dysferlinopathic muscle has been linked with an increase in C/EBPδ and PPARγ mRNA in the muscle. Both of these are essential transcription factors in adipocyte differentiation, and MMP-14 is suggested to one of the extracellular signals that triggers adipogenic differentiation of FAPs. MMP-14 is released by myofibers and is critical to successful myogenesis during muscle regeneration. MMP-14 expression in the dysferlin-null SJL mouse quadriceps increases by 3-fold between 2 month old (presymptomatic) and 9 month old (symptomatic) muscles. Similar analysis of SJL mice has identified that the levels of AnxA1 and AnxA2 increases as these mice transition from 2 to 8 months of age. Consistent with the putative role for MMP-14 in adipogenic conversion of dysferlinopathic muscle, pharmacological inhibition of MMP-14 (by batimastat) reduces FAP adipogenesis in vitro and ameliorates injury-triggered lipid formation in vivo (FIG. 11). This indicates that gradual loss of FAP ciliation and/or repression of the Hh pathway contributes to pro-adipogenic niche formation in dysferlinopathic muscle. Batimastat treatment has also been shown to reduce fibrosis and increase muscle function in mdx mice, which is reflective of an anti-fibrotic effect on FAPs in dystrophin-deficient muscle. Because batimastat broadly inhibits MMPs, it is not clear whether this is due to specific inhibition of MMP-14 or other MMPs upregulated in mdx muscle. But, it is clear that more insight into the mechanisms by which FAPs choose between fibrosis and adipogenesis and therapies targeting these pathways are of great interest in treating, preventing, reducing, and/or inhibiting a muscular degenerative condition muscular dystrophies and other degenerative muscle diseases.

AnxA2-mediated MMP secretion has been shown to cause joint destruction in rheumatoid arthritis, indicating AnxA2/MMP interactions plays a role in FAP-dependent adipogenesis in dysferlinopathic muscle. AnxA2 has also been shown to influence Hh signaling via the AnxA2 receptor in endothelial cells, providing additional mechanisms by which AnxA2 and MMP-14 may be linked during adipogenic niche formation in dysferlinopathic muscle. Such a role of AnxA2 is consistent with some studies showing that loss of AnxA2 uncouples the repair defect of dysferlinopathic myofibers from the eventual adipogenic replacement of the muscle, identifying AnxA2 and MMP-14 as therapeutic targets for LGMD2B. This represents a significant advance towards development of the therapy for this disease, which currently lacks any effective or approved therapy. Unlike other inflammatory muscle diseases, where suppression of inflammation with corticosteroids is effective, treatment of dysferlinopathic patients with glucocorticoids has been without success, which can be due to the role of conventional corticosteroids in inducing myofiber damage and activating FAP adipogenesis. Further, use of tyrosine kinase inhibitors prevent excessive FAP proliferation in DMD mouse model, have toxicity associated with their long-term use required for LGMD2B. The identification of inhibiting adipogenesis in dysferinopathic muscle by targeting FAPs by MMP-14 inhibitors (batimastat) also opens avenues for the use of other candidate drugs like promethazine, which also inhibits FAP adipogenesis. In principal, the direct manipulation of PDGFRα splicing by morpholinos can also be beneficial by preventing FAP proliferation. Irrespective of the precise therapeutic approach that is efficacious, the current disclosure shows the accumulation and adipogenic differentiation of FAPs as a central target to prevent the precipitation of cellular deficits into the abrupt onset of disease in dysferlinopathies. Moreover, such therapies will be complementary to the ongoing efforts to restore dysferlin expression in terminally differentiated myofibers.

Example 7. Methods

Patient Biopsies. Patient biopsies were obtained under informed consent and was approved by the Ethics Committee of Hospital de la Santa Creu i Sant Pau de Barcelona. Frozen muscle biopsies from LGMD2B patients with 2 confirmed mutations in dysferlin were used. These were classified mild, moderate and severe based on their clinical phenotype (Table 1) for analysis. As a control, frozen muscle biopsies were obtained from young adults with no known neuromuscular conditions and without any histopathological features to serve as a comparison.

Animals. All animal procedures were conducted in accordance with guidelines for the care and use of laboratory animals, and were approved by the Children's National Medical Center Institutional Animal Care and Use Committee. C57BL/6J (WT) and B6.A-Dysf$^{prmd}$/GeneJ (B6A/J) mice were obtained from the Jackson Laboratory (Bar Harbor, Me.) and maintained as homozygous colonies for the purpose of this study. A2-B6A/J mice were generated as part of our previous study, and are maintained in-house. All animals were maintained in an individually vented cage system under a controlled 12 h light/dark cycle with free access to food and water. Mice were used at the timepoints indicated in the study ±2 weeks.

Immunohistochemical Analysis of Muscle Sections. Frozen sections 8 μm thick were cut from human biopsies and the midbelly of mouse muscles. Lipid was visualized using an Oil Red O staining kit (American MasterTech, #KTORO) according to manufacturer's instructions. Immunofluorescence was performed by fixing sections in chilled 10% neutral buffered formalin, blocking with 5% BSA and incubation with primary antibodies against perilipin-1 (1:250, Sigma, #P1873), PDGFRα (1:250, Cell Signaling, #3174S), Annexin A2 (1:250, Santa Cruz, #SC-9061) and F4/80 (1:500, Serotec, #MCA497). For co-labeling anti-PDGFRα (1:100, R&D Systems, #AF1062) was used. Staining was visualized using relevant secondary antibodies conjugated to AlexaFluor 488 and/or 568 (1:500, ThermoFisher). Myofiber membranes were marked using AlexaFluor 488-conjugated wheat germ agglutinin (1:500, ThermoFisher, #W11261) and coverslips were mounted using ProLong Gold with DAPI (ThermoFisher, #P36941).

Microscopy and Image Analysis. Microscopy was performed using an Olympus BX61 VS120-S5 Virtual Slide Scanning System with UPlanSApo 40×/0.95 objective, Olympus XM10 monochrome camera or Allied vision Pike F-505C color camera, and Olympus VS-ASW FL 2.7 imaging software. Confocal images were acquired using an Olympus FV1000 Confocal Microscope with UPlanFLN 40×/1.30 oil objective and Olympus FV-ASW version 4.2 imaging software. Perilipin-1 quantification was performed by thresholding the image to exclude non-specific staining and then calculating the area of each lipid deposit encircled by perlipin-1 (excluding those in the epi- or perimysium) using MetaMorph software (Molecular Devices). The total area encircled by perilipin-1 was calculated for all lipid deposits across the muscle and expressed relative to the total cross-sectional area. PDGFRα and AnxA2 positive area was calculated using CellSens software (Olympus) by thresholding to remove non-specific staining and calculating the total positive area (again, excluding any epi- or perimysial staining) relative to the entire muscle cross-section.

Isolation and In Vitro Adipogenesis of FAPs. FAPs were isolated from the hindlimb muscles of 6Mo B6A/J mice in a modified protocol from previously published studies. Mice were euthanized and the tibialis anterior, extensor digitorum longus, gastrocnemius, soleus, quadriceps and psoas were immediately dissected. Non-muscle tissue including tendon, nerve and overlying fascia were carefully removed, and muscles were minced finely in a sterile dish and incubated in Collagenase II (2.5 U/ml, ThermoFisher, #17101015) in PBS for 30 min at 37° C. The resulting slurry was washed with sterile PBS before further digest in Collagenase D (1.5 U/ml, Sigma Aldridge, #COLLD-RO) and Dispase II (2.4 U/ml, Sigma Aldridge, #D4693) in PBS for 60 min at 37° C. Resulting slurries were passed through 100 μm and 40 μm strainers and primary cells were resuspended in 1 ml PBS with 2% FBS and 2 nM EDTA. 300 μl of the primary cell suspension was reserved for plating and the remaining was stained with anti-PDGFRα-APC (1.0 μg per $10^6$ cells in 100 μl, Biolegend, #135908) and isotype control (1.0 μg per $10^6$ cells in 100 μl, Biolegend, #400512) for FACS. Cells stained with isotype control were used as a control for gating positive and negative events. Cells stained with anti-PDGFRα-APC were then sorted on an Influx cell sorter (Becton Dickenson, #646500) using two-way sorting to separate positive and negative PDGFRα-expressing cells for further analysis (FIG. 14).

The freshly isolated primary cell, PDGFRα$^-$ and PDGFRα$^+$ populations were plated in Matrigel coated Nunc Lab-Tek chamber slides (ThermoFisher, #154534) at a density of 20,000 cells/well. Cells were cultured in DMEM (Lonza, #12-604F) supplemented with 20% fetal bovine serum, 1% penicillin and 2.5 ng/ml bFGF (BioLegend, #579604) for 3 days. Adipogenic differentiation was induced by exposure to DMEM with 10% FBS, 0.5 mM IBMX (Sigma Aldridge, #15879), 0.25 μM dexamethasone (Sigma Aldridge, # D2915) and 10 μg/ml insulin (Sigma Aldridge, #10516) for 3 days. Following this, cells were cultured in adipogenic maintenance media (DMEM with 10% FBS and 10 μg/ml insulin) for 3 days. Uninduced cells were not exposed to the adipogenic differentiation media, but instead cultured for 6 days in the adipogenic maintenance media, with the media changed after 3 days. At the beginning of day 10, cells were fixed for 30 min in chilled, neutral buffered formalin before Oil Red O staining to visualize lipid. For studies involving AnxA2 treatment, FAPs were isolated and plated as described above. From day 3 onwards, cells were continuously treated with 100 nM recombinant AnxA2 (RayBiotech, #230-30023) until being fixed for oil red staining on day 10.

Notexin Injury. Single injury was performed by carefully shaving the anterior hindlimb before intramuscular injection of 40 μl notexin (5 μg/mL, Latoxan, #L8104) into the tibialis anterior using a 0.3 ml ultrafine insulin syringe (BD Biosciences, #324906) Immediately prior to injection, the needle was dipped in green tattoo dye (Harvard Apparatus, #72-9384) to mark the needle track. The contralateral leg was left uninjured as a control. Mice were allowed to recover for 28 days before the animal was euthanized and muscles collected for analysis. For repeat injuries we performed 3 separate intramuscular notexin injections, each 14 days apart, and allowed 28 days of recovery following the final injury before tissue collection. Using the superficial mark on the skin from the tattoo dye, we attempted to perform each injury as close to the site of the previous injury as possible so as to repeatedly injure the same myofibers each time. For AnxA2-notexin studies, 10 μg recombinant AnxA2 (RayBiotech, #230-30023) was added to 40 μl notexin (5 μg/mL, Latoxan, #L8104) and injected into the mid-belly of the right tibialis anterior. The contralateral (left) tibialis anterior was injected with 40 μl notexin only for comparison. Again, these muscles were harvested for analysis 28 d after injury.

Batimastat Treatment. For in vitro studies, PDGFRα$^+$ FAPs were isolated from 12Mo B6A/J muscle as described above, and plated in Matrigel-coated Nunc Lab-Tek chamber slides at 40,000 cells/well. Cells were cultured in DMEM (Lonza, #12-604F) supplemented with 20% fetal bovine serum, 1% penicillin and 2.5 ng/ml bFGF (BioLegend, #579604) for 3 days. After which, cells were treated with 10 μM batimastat (Sigma-Aldridge, #SML0041) added to the adipogenic maintenance media for 6 days. At the beginning of day 10, cells were fixed for 30 min in chilled, neutral buffered formalin before Oil Red O staining to visualize lipid.

For in vivo studies, 12Mo B6A/J mice were treated thrice weekly with batimastat (Sigma-Aldridge, #SML0041), 2 mg/kg i.p. for 10 weeks. At the end of the treatment period, the effect of batimastat on disease pathology was evaluated by quantification of perilipin-1 marked lipid area in the gastrocnemius and compared to untreated controls. In addition, we tested injury-triggered adipogenesis using the repeat notexin injury protocol described above and in FIG. 12. During the 10 week treatment period 12Mo B6A/J mice were subjected to 3 intramuscular notexin injections into the TA, each 2 weeks apart, beginning on day 2 and ending on day 29. After 10 weeks of treatment, injury-induced lipid formation was quantified by perlipin-1 area in the injured TA and compared between batimastat treated and untreated controls. For both experiments, batimastat was first dissolved in DMSO, before being reconstituted in sterile 5% saline for treatment.

Statistical Analysis. Data were analyzed using Prism GraphPad software. The precise statistical test employed varied depending on the nature of the analysis and is listed in the legend for each figure.

What is claimed is:

1. A method of treating a muscular degenerative condition in a subject, said method comprising: administering to the subject an effective amount of a therapeutic agent that inhibits accumulation or adipogenesis of a fibro/adipogenic precursor (FAP) cell.

2. The method of claim 1, wherein the muscular degenerative condition comprises duchenne type muscular dystrophy, facioscapulohumeral muscular dystrophy (FSHD), age-related muscle weakness, muscular degeneration due to physical injury, disuse atrophy, or a limb-girdle muscular dystrophy.

3. The method of claim 2, wherein the limb-girdle muscular dystrophy is limb-girdle muscular dystrophy 2B.

4. The method of claim 2, wherein the age-related muscle weakness comprises sarcopenia.

5. The method of claim 2, wherein the physical injury comprises leg injury, ankle injury, hand injury, elbow injury, rotator cuff injury of the shoulder, or rotator cuff injury of the hip.

6. The method of claim 1, wherein the subject is a human.

7. The method of claim 1, wherein the therapeutic agent comprises an Annexin A2 inhibitor, a matrix metalloproteinase (MMP) inhibitor, or a Toll-like receptor (TLR)-4 inhibitor, or a combination thereof.

8. The method of claim 7, wherein the Annexin A2 inhibitor comprises a small molecule, an RNA interference (RNAi) modulator, a small molecule AnxA2 tetramer inhibitor, a morpholino, or an antibody or a functionally fragment thereof.

9. The method of claim 8, wherein the small molecule or peptide comprises Anx A2 inhibitors.

10. The method of claim 7, wherein the matrix metalloproteinase (MMP) inhibitor comprises a small molecule, an RNAi modulator, or an antibody or a functionally fragment thereof.

11. The method of claim 10, wherein the small molecule comprises promethazine.

12. The method of claim 7, wherein the TLR-4 inhibitor comprises a small molecule, an RNAi modulator, or an antibody or a functionally fragment thereof.

13. The method of claim 12, wherein the small molecule comprises Pepinh-MYD, TAK-242, Candesartan, Valsartan, Fluvastatin, Simvastatin, Atorvastatin, or ST2825.

14. The method of claim 1, further comprising administering to the subject one or more anti-inflammatory agents.

* * * * *